US012623078B2

(12) United States Patent
Papay et al.

(10) Patent No.: US 12,623,078 B2
(45) Date of Patent: May 12, 2026

(54) SYSTEM AND METHOD FOR TREATING OBSTRUCTIVE SLEEP APNEA

(71) Applicants: THE CLEVELAND CLINIC FOUNDATION, Cleveland, OH (US); XII MEDICAL, INC., Cleveland, OH (US)

(72) Inventors: Francis A. Papay, Westlake, OH (US); Anthony V. Caparso, North Ridgeville, OH (US)

(73) Assignees: The Cleveland Clinic Foundation, Cleveland, OH (US); XII Medical, Inc., Union City, CA (US)

( * ) Notice: Subject to any disclaimer, the term of this patent is extended or adjusted under 35 U.S.C. 154(b) by 0 days.

(21) Appl. No.: 18/462,278

(22) Filed: Sep. 6, 2023

(65) Prior Publication Data

US 2024/0066300 A1 Feb. 29, 2024

Related U.S. Application Data

(63) Continuation of application No. 16/507,390, filed on Jul. 10, 2019, now Pat. No. 11,771,899.
(Continued)

(51) Int. Cl.
*A61N 1/36* (2006.01)
*A61B 5/00* (2006.01)
(Continued)

(52) U.S. Cl.
CPC .......... *A61N 1/3611* (2013.01); *A61B 5/0826* (2013.01); *A61B 5/389* (2021.01);
(Continued)

(58) Field of Classification Search
CPC .. A61N 1/3611; A61N 1/378; A61N 1/36128; A61B 5/389; A61B 5/0826; A61B 5/4836; A61F 2002/2807
See application file for complete search history.

(56) References Cited

U.S. PATENT DOCUMENTS

| 910,774 A | 1/1909 | Beers |
| 4,990,160 A | 2/1991 | Terino |
| (Continued) | | |

FOREIGN PATENT DOCUMENTS

| EP | 3962593 B1 | 7/2023 |
| EP | 4241690 A2 | 9/2023 |
| (Continued) | | |

OTHER PUBLICATIONS

International Search Report and Written Opinion mailed Apr. 22, 2022; International Application No. PCT/US2022/070101; 15 pages.
(Continued)

*Primary Examiner* — Carl H Layno
*Assistant Examiner* — Aya Ziad Bakkar
(74) *Attorney, Agent, or Firm* — Fortem IP LLP

(57) ABSTRACT

One aspect of the present disclosure relates to a system for treating obstructive sleep apnea in a subject. The system can include a power source and a neuromuscular stimulator in electrical communications with the power source. The neuromuscular stimulator can include a controller and at least one electrode. The controller can be configured to receive certain power and stimulation parameters associated with a therapy signal from the power source. The at least one electrode can be configured to deliver the therapy signal to a target tissue associated with control of a posterior base of the tongue of the subject.

25 Claims, 14 Drawing Sheets

Related U.S. Application Data

(60) Provisional application No. 62/696,135, filed on Jul. 10, 2018.

(51) Int. Cl.

| | |
|---|---|
| *A61B 5/08* | (2006.01) |
| *A61B 5/389* | (2021.01) |
| *A61N 1/378* | (2006.01) |
| *A61F 2/28* | (2006.01) |

(52) U.S. Cl.
CPC ......... *A61N 1/36128* (2013.01); *A61N 1/378* (2013.01); *A61B 5/4836* (2013.01); *A61F 2002/2807* (2013.01)

(56) References Cited

U.S. PATENT DOCUMENTS

| | | | |
|---|---|---|---|
| 5,335,657 A | 8/1994 | Terry et al. | |
| 5,522,862 A | 6/1996 | Testerman et al. | |
| 5,591,216 A | 1/1997 | Testerman et al. | |
| 5,609,621 A | 3/1997 | Bonner | |
| 5,716,377 A | 2/1998 | Rise et al. | |
| 5,877,466 A | 3/1999 | Bolongeat-Mobleu et al. | |
| 5,988,171 A | 11/1999 | Sohn et al. | |
| 6,240,316 B1 | 5/2001 | Richmond et al. | |
| 6,314,324 B1 | 11/2001 | Lattner et al. | |
| 6,345,202 B2 | 2/2002 | Richmond et al. | |
| 6,587,725 B1 | 7/2003 | Durand et al. | |
| 6,770,022 B2 | 8/2004 | Mechlenburg et al. | |
| 7,660,632 B2 | 2/2010 | Kirby et al. | |
| 7,668,591 B2 | 2/2010 | Lee et al. | |
| 7,680,538 B2 | 3/2010 | Durand et al. | |
| 7,711,438 B2 | 5/2010 | Lattner et al. | |
| 7,885,713 B2 | 2/2011 | Campbell et al. | |
| 8,204,602 B2 | 6/2012 | Kallmyer | |
| 8,255,056 B2 | 8/2012 | Tehrani | |
| 8,498,712 B2 | 7/2013 | Bolea et al. | |
| 8,498,713 B2 | 7/2013 | McClure et al. | |
| 8,574,164 B2 | 11/2013 | Mashiach | |
| 8,577,464 B2 | 11/2013 | Mashiach | |
| 8,577,465 B2 | 11/2013 | Mashiach | |
| 8,577,466 B2 | 11/2013 | Mashiach | |
| 8,577,467 B2 | 11/2013 | Mashiach et al. | |
| 8,577,468 B2 | 11/2013 | Mashiach et al. | |
| 8,577,472 B2 | 11/2013 | Mashiach et al. | |
| 8,577,478 B2 | 11/2013 | Mashiach et al. | |
| 8,577,647 B2 | 11/2013 | Farritor et al. | |
| 8,585,617 B2 | 11/2013 | Mashiach et al. | |
| 8,588,941 B2 | 11/2013 | Mashiach | |
| 8,626,304 B2 | 1/2014 | Bolea et al. | |
| 8,644,957 B2 | 2/2014 | Mashiach | |
| 8,700,183 B2 | 4/2014 | Mashiach | |
| 8,718,776 B2 | 5/2014 | Mashiach et al. | |
| 8,744,589 B2 | 6/2014 | Bolea et al. | |
| 8,751,005 B2 | 6/2014 | Meadows et al. | |
| 8,798,773 B2 | 8/2014 | Mashiach | |
| 8,812,113 B2 | 8/2014 | Mashiach | |
| 8,812,135 B2 | 8/2014 | Mashiach | |
| 8,831,730 B2 | 9/2014 | Mashiach et al. | |
| 8,838,256 B2 | 9/2014 | Mashiach et al. | |
| 8,897,880 B2 | 11/2014 | Mashiach | |
| 8,897,895 B2 | 11/2014 | Mashiach | |
| 8,903,493 B2 | 12/2014 | Mashiach et al. | |
| 8,903,515 B2 | 12/2014 | Mashiach | |
| 8,948,871 B2 | 2/2015 | Mashiach et al. | |
| 8,958,893 B2 | 2/2015 | Mashiach | |
| 8,989,868 B2 | 3/2015 | Mashiach et al. | |
| 9,031,653 B2 | 5/2015 | Mashiach | |
| 9,031,654 B2 | 5/2015 | Meadows et al. | |
| 9,044,612 B2 | 6/2015 | Mashiach et al. | |
| 9,061,151 B2 | 6/2015 | Mashiach et al. | |
| 9,061,162 B2 | 6/2015 | Mashiach et al. | |
| 9,095,725 B2 | 8/2015 | Mashiach | |
| 9,101,774 B2 | 8/2015 | Mashiach et al. | |
| 9,155,899 B2 | 10/2015 | Mashiach et al. | |
| 9,186,511 B2 | 11/2015 | Bolea | |
| 9,220,907 B2 | 12/2015 | Maschiach et al. | |
| 9,220,908 B2 | 12/2015 | Mashiach | |
| 9,248,290 B2 | 2/2016 | Mashiach | |
| 9,248,291 B2 | 2/2016 | Mashiach | |
| 9,248,302 B2 | 2/2016 | Mashiach et al. | |
| 9,259,585 B2 | 2/2016 | Vajha et al. | |
| 9,302,093 B2 | 4/2016 | Mashiach | |
| 9,308,370 B2 | 4/2016 | Lima et al. | |
| 9,308,381 B2 | 4/2016 | Mashiach et al. | |
| 9,314,613 B2 | 4/2016 | Mashiach | |
| 9,314,641 B2 | 4/2016 | Meadows et al. | |
| 9,327,132 B2 | 5/2016 | Mashiach | |
| 9,339,651 B2 | 5/2016 | Meadows et al. | |
| 9,358,392 B2 | 6/2016 | Mashiach | |
| 9,370,657 B2 * | 6/2016 | Tehrani ............... A61N 1/3611 |
| 9,393,435 B2 | 7/2016 | Mashiach | |
| 9,403,009 B2 | 8/2016 | Mashiach | |
| 9,403,025 B2 | 8/2016 | Mashiach et al. | |
| 9,409,013 B2 | 8/2016 | Mashiach et al. | |
| 9,415,215 B2 | 8/2016 | Mashiach | |
| 9,415,216 B2 | 8/2016 | Mashiach | |
| 9,421,372 B2 | 8/2016 | Mashiach et al. | |
| 9,463,318 B2 | 10/2016 | Mashiach et al. | |
| 9,486,628 B2 | 11/2016 | Christopherson et al. | |
| 9,757,560 B2 | 9/2017 | Papay | |
| 9,849,288 B2 | 12/2017 | Meadows et al. | |
| 9,913,982 B2 | 3/2018 | Bolea et al. | |
| 9,950,166 B2 | 4/2018 | Mashiach et al. | |
| 10,029,098 B2 | 7/2018 | Papay | |
| 10,065,038 B2 | 9/2018 | Papay | |
| 10,105,538 B2 | 10/2018 | Bolea et al. | |
| 10,238,468 B2 | 3/2019 | Forsell | |
| 10,675,467 B2 | 6/2020 | Papay | |
| 11,000,223 B2 | 5/2021 | Ser et al. | |
| 11,081,222 B2 | 8/2021 | Hoegh et al. | |
| 11,266,838 B1 | 3/2022 | Tehrani | |
| 11,291,842 B2 | 4/2022 | Caparso et al. | |
| 11,338,142 B2 | 5/2022 | Papay | |
| 11,351,377 B2 | 6/2022 | Papay et al. | |
| 11,351,380 B2 | 6/2022 | Caparso et al. | |
| 11,420,061 B2 | 8/2022 | Caparso et al. | |
| 11,420,063 B2 | 8/2022 | Caparso et al. | |
| 11,491,333 B2 | 11/2022 | Papay | |
| 11,691,010 B2 | 7/2023 | Caparso et al. | |
| 11,712,565 B2 | 8/2023 | Papay | |
| 11,771,899 B2 | 10/2023 | Papay et al. | |
| 11,869,211 B2 | 1/2024 | Caparso et al. | |
| 11,883,667 B2 | 1/2024 | Caparso et al. | |
| 12,172,013 B2 | 12/2024 | Caparso et al. | |
| 12,434,058 B2 | 10/2025 | Papay | |
| 12,491,366 B2 | 12/2025 | Caparso | |
| 2002/0010495 A1 | 1/2002 | Tucker et al. | |
| 2005/0076908 A1 | 4/2005 | Lee et al. | |
| 2006/0122662 A1 | 6/2006 | Tehrani et al. | |
| 2006/0224211 A1 | 10/2006 | Durand et al. | |
| 2007/0160274 A1 | 7/2007 | Mashiach | |
| 2007/0239230 A1 | 10/2007 | Giftakis et al. | |
| 2007/0263915 A1 | 11/2007 | Mashiach | |
| 2008/0039904 A1 | 2/2008 | Beutler et al. | |
| 2008/0082147 A1 | 4/2008 | Dai et al. | |
| 2008/0260217 A1 | 10/2008 | Mashiach | |
| 2008/0260229 A1 | 10/2008 | Mashiach | |
| 2009/0082831 A1 | 3/2009 | Paul et al. | |
| 2009/0226057 A1 | 9/2009 | Mashiach et al. | |
| 2009/0270960 A1 | 10/2009 | Zhao et al. | |
| 2010/0016749 A1 | 1/2010 | Atsma et al. | |
| 2010/0094379 A1 | 4/2010 | Meadows et al. | |
| 2010/0174341 A1 | 7/2010 | Bolea et al. | |
| 2010/0179562 A1 | 7/2010 | Linker et al. | |
| 2010/0241195 A1 | 9/2010 | Meadows et al. | |
| 2010/0260217 A1 | 10/2010 | Redford | |
| 2010/0280568 A1 | 11/2010 | Bulkes et al. | |
| 2010/0292769 A1 | 11/2010 | Brounstein et al. | |
| 2011/0071606 A1 | 3/2011 | Kast et al. | |
| 2011/0093032 A1 | 4/2011 | Boggs et al. | |
| 2011/0093034 A1 | 4/2011 | Miller et al. | |
| 2011/0093036 A1 | 4/2011 | Mashiach | |

(56)  References Cited

U.S. PATENT DOCUMENTS

| 2011/0125212 A1 | 5/2011 | Tyler |
|---|---|---|
| 2011/0137376 A1 | 6/2011 | Meskens |
| 2011/0230702 A1 | 9/2011 | Honour |
| 2012/0010532 A1 | 1/2012 | Bolea et al. |
| 2012/0010681 A1 | 1/2012 | Bolea et al. |
| 2013/0085537 A1 | 4/2013 | Mashiach |
| 2013/0085558 A1 | 4/2013 | Mashiach |
| 2013/0204097 A1 | 8/2013 | Rondoni et al. |
| 2013/0289401 A1 | 10/2013 | Colbaugh et al. |
| 2014/0031840 A1 | 1/2014 | Mashiach |
| 2014/0031902 A1 | 1/2014 | Mashiach et al. |
| 2014/0031903 A1 | 1/2014 | Mashiach |
| 2014/0031904 A1 | 1/2014 | Mashiach |
| 2014/0046221 A1 | 2/2014 | Mashiach et al. |
| 2014/0052219 A1 | 2/2014 | Mashiach et al. |
| 2014/0100642 A1 | 4/2014 | Mashiach |
| 2014/0135868 A1 | 5/2014 | Bashyam |
| 2014/0172061 A1 | 6/2014 | Mashiach |
| 2014/0228905 A1 | 8/2014 | Bolea |
| 2014/0266933 A1 | 9/2014 | Andersen et al. |
| 2014/0358026 A1 | 12/2014 | Mashiach et al. |
| 2014/0358189 A1 | 12/2014 | Mashiach et al. |
| 2014/0358196 A1 | 12/2014 | Mashiach |
| 2014/0358197 A1 | 12/2014 | Mashiach et al. |
| 2014/0371802 A1 | 12/2014 | Mashiach et al. |
| 2014/0371817 A1 | 12/2014 | Mashiach et al. |
| 2014/0379049 A1 | 12/2014 | Mashiach et al. |
| 2015/0032177 A1 | 1/2015 | Mashiach et al. |
| 2015/0077308 A1 | 3/2015 | Jeon et al. |
| 2015/0088025 A1 | 3/2015 | Litvak et al. |
| 2015/0096167 A1 | 4/2015 | Zhao et al. |
| 2015/0112402 A1 | 4/2015 | Mashiach |
| 2015/0112416 A1 | 4/2015 | Mashiach et al. |
| 2015/0142120 A1 | 5/2015 | Papay |
| 2015/0196766 A1 | 7/2015 | Rosenberg et al. |
| 2015/0224307 A1* | 8/2015 | Bolea ................. A61N 1/36057 607/42 |
| 2015/0265221 A1 | 9/2015 | Flanagan et al. |
| 2015/0283313 A1 | 10/2015 | Huber |
| 2015/0290454 A1 | 10/2015 | Tyler et al. |
| 2015/0290465 A1 | 10/2015 | Mashiach |
| 2015/0343221 A1 | 12/2015 | Mashiach |
| 2016/0094082 A1 | 3/2016 | Ookawa et al. |
| 2016/0106976 A1 | 4/2016 | Kucklick |
| 2016/0121121 A1 | 5/2016 | Mashiach |
| 2016/0121122 A1 | 5/2016 | Mashiach |
| 2016/0166828 A1 | 6/2016 | Yu |
| 2016/0175587 A1 | 6/2016 | Lima et al. |
| 2016/0184583 A1 | 6/2016 | Meadows et al. |
| 2016/0235990 A1 | 8/2016 | Mashiach |
| 2016/0287863 A1 | 10/2016 | Mercanzini et al. |
| 2016/0346537 A1 | 12/2016 | Mashiach |
| 2017/0087360 A1 | 3/2017 | Scheiner |
| 2017/0106190 A1* | 4/2017 | Papay ................... A61N 1/3601 |
| 2017/0143257 A1 | 5/2017 | Kent et al. |
| 2017/0143280 A1 | 5/2017 | Kent et al. |
| 2017/0274210 A1 | 9/2017 | Papay |
| 2017/0290699 A1 | 10/2017 | Radmand |
| 2017/0296815 A1 | 10/2017 | Papay |
| 2018/0015282 A1 | 1/2018 | Waner et al. |
| 2018/0028824 A1 | 2/2018 | Pivonka et al. |
| 2018/0117313 A1 | 5/2018 | Schmidt et al. |
| 2018/0191069 A1 | 7/2018 | Chen et al. |
| 2018/0221673 A1 | 8/2018 | Kuang |
| 2018/0280694 A1 | 10/2018 | Mashiach et al. |
| 2019/0117966 A1 | 4/2019 | Kent |
| 2019/0247664 A1 | 8/2019 | Irazoqui et al. |
| 2020/0016401 A1 | 1/2020 | Papay et al. |
| 2020/0269044 A1 | 8/2020 | Papay |
| 2020/0338358 A1 | 10/2020 | Makansi |
| 2020/0346010 A1 | 11/2020 | Papay et al. |
| 2020/0346016 A1 | 11/2020 | Caparso et al. |
| 2020/0346017 A1 | 11/2020 | Caparso et al. |
| 2020/0346024 A1 | 11/2020 | Caparso et al. |
| 2021/0106824 A1 | 4/2021 | Caparso et al. |
| 2021/0128914 A1 | 5/2021 | Papay |
| 2021/0228867 A1 | 7/2021 | Scheiner et al. |
| 2022/0134101 A1 | 5/2022 | Scheiner et al. |
| 2022/0218988 A1 | 7/2022 | Caparso et al. |
| 2022/0241588 A1 | 8/2022 | Caparso et al. |
| 2022/0266030 A1 | 8/2022 | Caparso et al. |
| 2022/0288390 A1 | 9/2022 | Papay et al. |
| 2022/0323752 A1 | 10/2022 | Papay |
| 2022/0370798 A1 | 11/2022 | Caparso et al. |
| 2022/0401738 A1 | 12/2022 | Caparso et al. |
| 2023/0024498 A1 | 1/2023 | Caparso et al. |
| 2023/0172479 A1 | 6/2023 | Verzal et al. |
| 2023/0277843 A1 | 9/2023 | Caparso et al. |
| 2023/0310860 A1 | 10/2023 | Papay |
| 2024/0108899 A1 | 4/2024 | Caparso et al. |
| 2024/0165411 A1 | 5/2024 | Caparso et al. |
| 2024/0198108 A1 | 6/2024 | Caparso et al. |
| 2024/0252820 A1 | 8/2024 | Keenan |
| 2025/0065119 A1 | 2/2025 | Caparso et al. |
| 2025/0195893 A1 | 6/2025 | Caparso et al. |

FOREIGN PATENT DOCUMENTS

| EP | 3962585 B1 | 5/2024 |
|---|---|---|
| EP | 4431008 A2 | 9/2024 |
| JP | 2013208182 A | 10/2013 |
| JP | 2013543741 A | 12/2013 |
| JP | 2019503722 A | 2/2019 |
| WO | 9219318 A1 | 11/1992 |
| WO | 2005018737 A1 | 3/2005 |
| WO | 2007080579 A2 | 7/2007 |
| WO | 2007080579 A3 | 7/2007 |
| WO | 2007080580 A2 | 7/2007 |
| WO | 2007080580 A3 | 7/2007 |
| WO | 2008129545 A1 | 10/2008 |
| WO | 2009007896 A2 | 1/2009 |
| WO | 2009007896 A3 | 1/2009 |
| WO | 2009109971 A2 | 9/2009 |
| WO | 2009109971 A3 | 9/2009 |
| WO | 2009143560 A1 | 12/2009 |
| WO | 2010006218 A2 | 1/2010 |
| WO | 2011048590 A1 | 4/2011 |
| WO | 2011077433 A1 | 6/2011 |
| WO | 2013046032 A2 | 4/2013 |
| WO | 2013046032 A3 | 4/2013 |
| WO | 2013046035 A2 | 4/2013 |
| WO | 2013046035 A3 | 4/2013 |
| WO | 2013046038 A2 | 4/2013 |
| WO | 2013046038 A3 | 4/2013 |
| WO | 2013046039 A2 | 4/2013 |
| WO | 2013046039 A3 | 4/2013 |
| WO | 2013046040 A2 | 4/2013 |
| WO | 2013046040 A3 | 4/2013 |
| WO | 2013046042 A2 | 4/2013 |
| WO | 2013046042 A3 | 4/2013 |
| WO | 2013046043 A2 | 4/2013 |
| WO | 2013046043 A3 | 4/2013 |
| WO | 2013046044 A2 | 4/2013 |
| WO | 2013046044 A3 | 4/2013 |
| WO | 2013046048 A2 | 4/2013 |
| WO | 2013046048 A3 | 4/2013 |
| WO | 2013046049 A2 | 4/2013 |
| WO | 2013046049 A3 | 4/2013 |
| WO | 2013046053 A2 | 4/2013 |
| WO | 2013046053 A3 | 4/2013 |
| WO | 2013057594 A2 | 4/2013 |
| WO | 2013057594 A3 | 4/2013 |
| WO | 2013057597 A1 | 4/2013 |
| WO | 2013061164 A2 | 5/2013 |
| WO | 2013061164 A3 | 5/2013 |
| WO | 2013061169 A2 | 5/2013 |
| WO | 2013061169 A3 | 5/2013 |
| WO | 2013177621 A1 | 12/2013 |
| WO | 2014016684 A2 | 1/2014 |
| WO | 2014016684 A3 | 1/2014 |
| WO | 2014016686 A2 | 1/2014 |
| WO | 2014016686 A3 | 1/2014 |
| WO | 2014016687 A2 | 1/2014 |
| WO | 2014016687 A3 | 1/2014 |

(56) References Cited

FOREIGN PATENT DOCUMENTS

| WO | 2014016688 A2 | 1/2014 |
| WO | 2014016688 A3 | 1/2014 |
| WO | 2014016691 A2 | 1/2014 |
| WO | 2014016691 A3 | 1/2014 |
| WO | 2014016692 A2 | 1/2014 |
| WO | 2014016692 A3 | 1/2014 |
| WO | 2014016693 A2 | 1/2014 |
| WO | 2014016693 A3 | 1/2014 |
| WO | 2014016694 A2 | 1/2014 |
| WO | 2014016694 A3 | 1/2014 |
| WO | 2014016697 A2 | 1/2014 |
| WO | 2014016697 A3 | 1/2014 |
| WO | 2014016700 A2 | 1/2014 |
| WO | 2014016700 A3 | 1/2014 |
| WO | 2014016701 A2 | 1/2014 |
| WO | 2014016701 A3 | 1/2014 |
| WO | 2014047310 A1 | 3/2014 |
| WO | 2014049448 A2 | 4/2014 |
| WO | 2014049448 A3 | 4/2014 |
| WO | 2014057361 A2 | 4/2014 |
| WO | 2014057361 A3 | 4/2014 |
| WO | 2014096969 A2 | 6/2014 |
| WO | 2014096969 A3 | 6/2014 |
| WO | 2014096971 A2 | 6/2014 |
| WO | 2014096973 A2 | 6/2014 |
| WO | 2014096973 A3 | 6/2014 |
| WO | 2014207576 A2 | 12/2014 |
| WO | 2014207576 A3 | 12/2014 |
| WO | 2015004540 A2 | 1/2015 |
| WO | 2015004540 A3 | 1/2015 |
| WO | WO 2015/073232 | 3/2015 |
| WO | 2015077283 A1 | 5/2015 |
| WO | WO 2015/224307 | 8/2015 |
| WO | 2015139053 A1 | 9/2015 |
| WO | 2017087681 A1 | 5/2017 |
| WO | 2017112960 A1 | 6/2017 |
| WO | 2017173433 A1 | 10/2017 |
| WO | WO 2018/200512 | 7/2018 |
| WO | WO 2019/151656 | 5/2019 |
| WO | WO 2019/160282 | 5/2019 |
| WO | 2020223723 A1 | 11/2020 |
| WO | 2020223738 A1 | 11/2020 |
| WO | 2020223740 A1 | 11/2020 |
| WO | 2021076188 A1 | 4/2021 |
| WO | 2021242633 A1 | 12/2021 |
| WO | 2022020489 A1 | 1/2022 |
| WO | 2022155632 A1 | 7/2022 |
| WO | 2024073487 A1 | 4/2024 |
| WO | 2024112826 A1 | 5/2024 |

OTHER PUBLICATIONS

International Search Report and Written Opinion mailed Feb. 26, 2024, International Application No. PCT/US2023/075231, 21 pages.
International Search Report and Written Opinion mailed May 6, 2024; International Application No. PCT/US2023/080808; 19 pages.
International Search Report and Written Opinion mailed Aug. 14, 2020, International Application No. PCT/US2020/031279, 19 pages.
International Search Report and Written Opinion mailed Feb. 10, 2015, International Application No. PCT/US2014/066311, 8 pages.
International Search Report and Written Opinion mailed Oct. 9, 2020, International Application No. PCT/US2020/031383, 13 pages.
International Search Report and Written Opinion mailed Sep. 7, 2020, International Application No. PCT/US2020/031266, 8 pages.
International Search Report and Written Opinion mailed Sep. 8, 2020, International Application No. PCT/US2020/031389, 9 pages.
Adachi, S. , et al., "Genioglossus muscle activity and inspiratory timing in obstructive sleep apnea", American Journal of Orthodontics & Dentofacial Orthopedics, Elsevier, Amsterdam, NL, vol. 104, No. 2, Aug. 1, 1993 (Aug. 1, 1993), pp. 138-145.
Bailey, "Activities of human genioglossus motor units", Respiratory Physiology & Neurobiology 179:14-22, 2011.

Björninen, Toni , et al., "The Effect of Fabrication Method on Passive UHF RFID Tag Performance", International Journal of Antennas and Propagation, https://doi.org/10.1155/2009/920947, 2009, 8 pages.
Cienfuegos, et al., "Mandible—Surgical approach", Intraocular—AO Surgery Reference, v1 .0 2008-12-01—(Accessed Apr. 18, 2016).
Cienfuegos, et al., "Mandible—Surgical approach", Submental—AO Surgery Reference, v1 .0 2008-12-01—(Accessed Apr. 18, 2016).
Decker, Michael J., et al., "Functional electrical stimulation and respiration during sleep", Departments of Medicine, Pulmonary and Critical Care, Radiology, and Biomedical Engineering University Hospitals of Cleveland and Case Western Reserve University on Aug. 7, 2018; pp. 1-9.
Fairbanks, David W., et al., "Neurostimulation for Obstructive Sleep Apnea: Investigations", ENT Journal• Jan. 1993; vol. 72, No. 1; pp. 1-6.
Goding, Jr., George S., et al., "Relief of Upper Airway Obstruction With Hypoglossal Nerve Stimulation in the Canine", Laryngoscope 108: Feb. 1998; pp. 162-169.
Katz, Eliot S., et al., "Genioglossus activity during sleep in normal control subjects and children with obstructive sleep apnea", Am J Respir Crit Care Med. Sep. 1, 2004;170(5):553-60 (Year: 2004).
Schwartz , et al., "Electrical Stimulation of the Lingual Musculature in Obstructive Sleep Apnea", Journal of Applied Physiology 81:643-652, 1996.
Tran, W. H., et al., "Development of Asynchronous, Intralingual Electrical Stimulation to Treat Obstructive Sleep Apnea", Proceedings of the 25th Annual International Conference of the IEEE EMBS Cancun, Mexico Sep. 17-21, 2003; pp. 375-378.
Tran, W. H., et al., "First Subject Evaluated with Simulated BIONTM Treatment in Posterior Genioglossus to Prevent Obstructive Sleep Apnea", Proceedings of the 26th Annual International Conference of the IEEE EMBS San Francisco, CA, USA, Sep. 1-5, 2004; pp. 4287-4289.
Yoo, Paul B., et al., "Effects of selective hypoglossal nerve stimulation on canine upper airway mechanics", J Appl Physiol 99: 937-943, 2005; published Apr. 14, 2005; pp. 937-943.
Adachi, et al., "Genioglossus muscle activity and inspiratory timing in obstructive sleep apnea", American Journal of Orthodontics & Dentofacial Orthopedics, Elsevier, Amsterdam, NL, vol. 104, No. 2, Aug. 1, 1993 (Aug. 1, 1993), pp. 138-145.
Björninen, et al., "The Effect of Fabrication Method on Passive UHF RFID Tag Performance", International Journal of Antennas and Propagation, https://doi.org/10.1155/2009/920947, 2009, 8 pages.
Cienfuegos, et al., "Mandible—Surgical approach", Intraocular—AO Surgery Reference, v1 .0 Dec. 1, 2008—(Accessed Apr. 18, 2016), (Accessed Apr. 18, 2016, Available at https://www2.aofoundation.org/wps/portal/surgery?showPage=approach&contentUrl=srg/91/04-Approaches/A12_intraoral_appr_ramus_cond.jsp&bone=CMF&segment=Mandible&approach=Intraoral).
Cienfuegos, et al., "Mandible—Surgical approach", Submental—AO Surgery Reference, v1 .0 Dec. 1, 2008—(Accessed Apr. 18, 2016), Available at https://www2.aofoundation. org/wps/portal/surgery?showPage=approach&contentUrl=srg/91/04-Approaches/A50_Submental.jsp&bone=CMF&segment=Mandible&approach=Submental).
Decker, et al., "Functional electrical stimulation and respiration during sleep", Departments of Medicine, Pulmonary and Critical Care, Radiology, and Biomedical Engineering University Hospitals of Cleveland and Case Western Reserve University on Aug. 7, 2018; pp. 1-9.
Fairbanks, et al., "Neurostimulation for Obstructive Sleep Apnea: Investigations", ENT Journal• Jan. 1993; vol. 72, No. 1; pp. 1-6.
Goding, Jr., et al., "Relief of Upper Airway Obstruction With Hypoglossal Nerve Stimulation in the Canine", Laryngoscope 108: Feb. 1998; pp. 162-169.
Katz, et al., "Genioglossus activity during sleep in normal control subjects and children with obstructive sleep apnea", Am J Respir Crit Care Med. Sep. 1, 2004;170(5):553-60 (Year: 2004).
Tran, et al., "Development of Asynchronous, Intralingual Electrical Stimulation to Treat Obstructive Sleep Apnea", Proceedings of the

(56) References Cited

OTHER PUBLICATIONS

25th Annual International Conference of the IEEE EMBS Cancun, Mexico Sep. 17-21, 2003; pp. 375-378.

Tran, et al., "First Subject Evaluated with Simulated BIONTM Treatment in Posterior Genioglossus to Prevent Obstructive Sleep Apnea", Proceedings of the 26th Annual International Conference of the IEEE EMBS San Francisco, CA, USA, Sep. 1-5, 2004; pp. 4287-4289.

Yoo, et al., "Effects of selective hypoglossal nerve stimulation on canine upper airway mechanics", J Appl Physiol 99: 937-943, 2005; published Apr. 14, 2005; pp. 937-943.

* cited by examiner

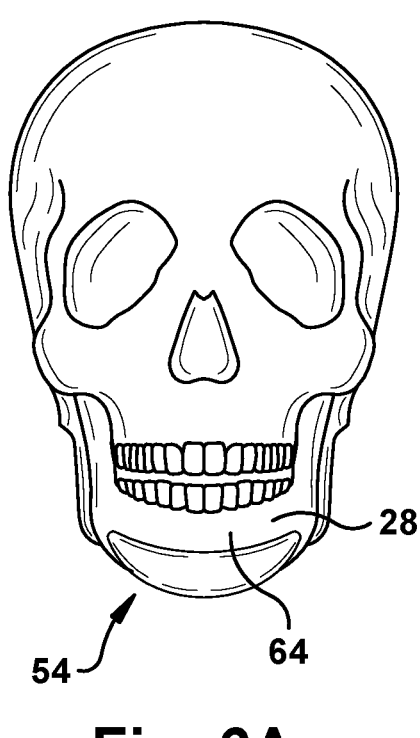
28
54     64
Fig. 6A
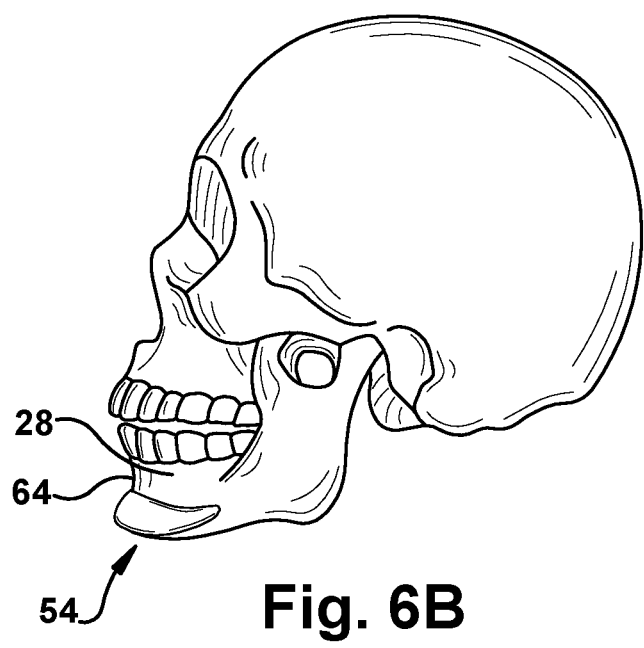
28
64
54     Fig. 6B

30

PROVIDING A SYSTEM COMPRISING A POWER SOURCE AND A NEUROMUSCULAR STIMULATOR — 32

IMPLANTING THE NEUROMUSCULAR STIMULATOR IN A SUBJECT SUFFERING FROM OBSTRUCTIVE SLEEP APNEA (OSA) — 34

ACTIVATING THE SYSTEM TO TREAT THE OSA — 36

80

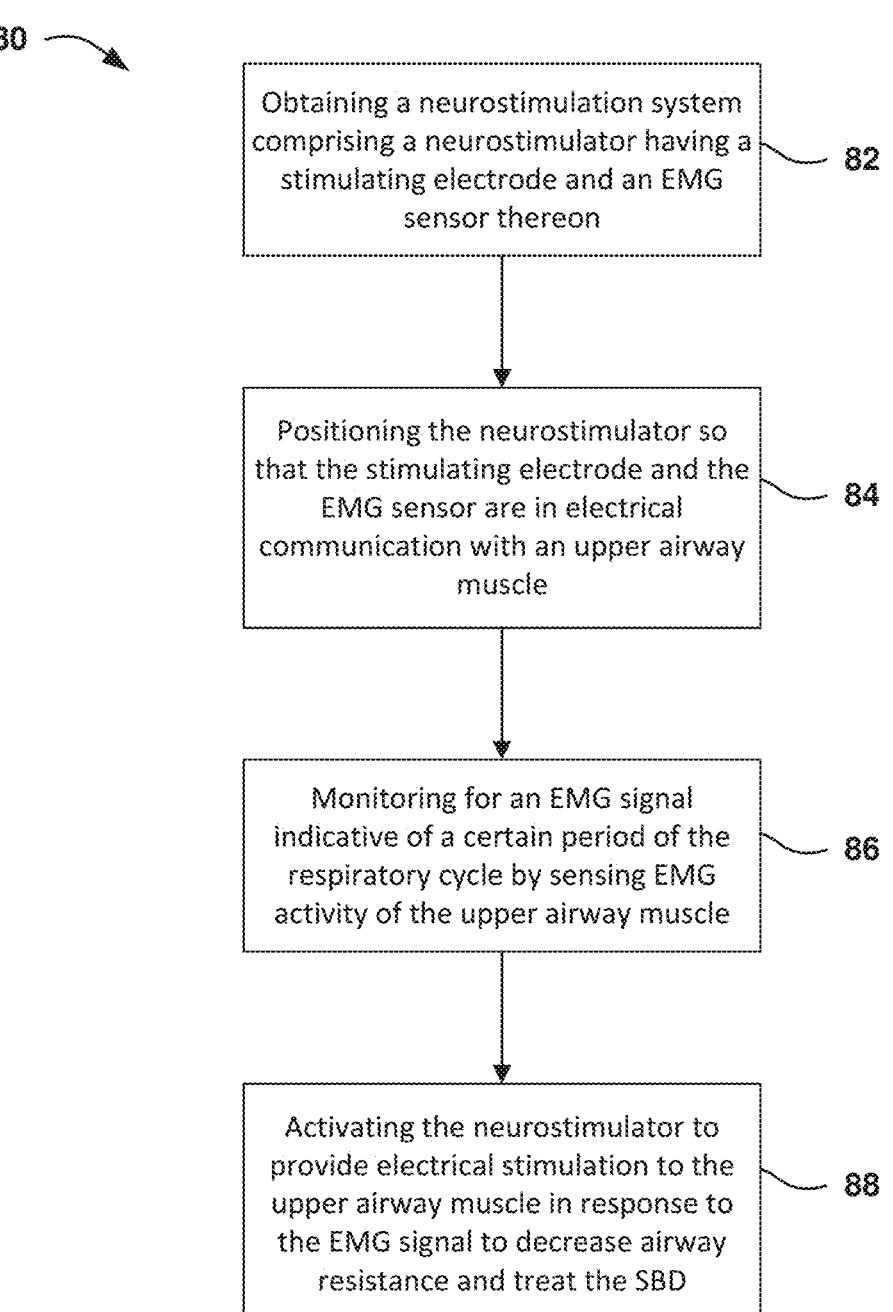

Obtaining a neurostimulation system comprising a neurostimulator having a stimulating electrode and an EMG sensor thereon — 82

Positioning the neurostimulator so that the stimulating electrode and the EMG sensor are in electrical communication with an upper airway muscle — 84

Monitoring for an EMG signal indicative of a certain period of the respiratory cycle by sensing EMG activity of the upper airway muscle — 86

Activating the neurostimulator to provide electrical stimulation to the upper airway muscle in response to the EMG signal to decrease airway resistance and treat the SBD — 88

Fig. 12

SYSTEM AND METHOD FOR TREATING OBSTRUCTIVE SLEEP APNEA

RELATED APPLICATIONS

This application is a continuation of U.S. application Ser. No. 16/507,390 filed on Jul. 10, 2019, now U.S. Pat. No. 11,771,899, which claims priority to U.S. Provisional Application No. 62/696,135 filed on Jul. 10, 2018, the entirety of each of which is incorporated by reference herein.

TECHNICAL FIELD

The present disclosure relates generally to a system and method for treating sleep disorders and, more particularly, to a system and method for treating obstructive sleep apnea.

BACKGROUND

Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc. Continuous positive airway pressure (CPAP) is a standard treatment for OSA. While CPAP is non-invasive and highly effective, it is not well tolerated by patients or sleeping partners. Patient compliance for CPAP is often reported to be between 40% and 60%. Surgical treatment options for OSA, such as anterior tongue muscle repositioning, orthognathic bimaxillary advancement, uvula-palatal-pharyngoplasty, and tracheostomy are available too. However, they tend to be highly invasive (result in structural changes), are irreversible, and have poor and/or inconsistent efficacy. Even the more effective surgical procedures are undesirable because they usually require multiple invasive and irreversible operations, they may alter a patient's appearance (e.g., maxillo-mandibulary advancement), and/or they may be socially stigmatic (e.g., tracheostomy) and have extensive morbidity.

SUMMARY

The present disclosure relates generally to a system and methods for treating sleep disorders and, more particularly, to a system and methods for treating obstructive sleep apnea (OSA).

One aspect of the present disclosure relates to a system for treating OSA in a subject. The system can comprise a power source and a neuromuscular stimulator in electrical communication with the power source. The neuromuscular stimulator can include a controller and at least one electrode. The controller can be configured to receive certain power and stimulation parameters associated with a therapy signal from the power source. The at least one electrode can be configured to deliver the therapy signal to a target tissue associated with control of a posterior base and lingual positioning of the tongue of the subject.

Another aspect of the present disclosure relates to a method for treating OSA in a subject. One step of the method can include providing a system comprising a power source and a neuromuscular stimulator in electrical communication with the power source. The neuromuscular stimulator can include a controller and at least one electrode. The controller can be configured to receive certain power and stimulation parameters associated with a therapy signal from the power source. Next, the neuromuscular stimulator can be implanted in the subject so that the at least one electrode is in electrical communication with a target tissue associated with direct or indirect control of a posterior base of the tongue and posterior oropharyngeal airway of the subject. The power source can then be activated so that the therapy signal is delivered to the at least one electrode for a time and in an amount sufficient to open the oropharyngeal airway to the laryngeal introitus.

Another aspect of the present disclosure relates to a method for treating OSA in a subject. One step of the method can include providing a closed-loop system comprising a power source, a neuromuscular stimulator, and a sensing component. The neuromuscular stimulator can be in electrical communication with the power source. The neuromuscular stimulator can include a controller and at least one electrode. The controller can be configured to receive certain power and data associated with a therapy signal from the power source. The sensing component can be configured to detect at least one physiological parameter or a related symptom associated with OSA. Next, the system can be implanted in the subject so that the at least one electrode and the sensing component are in electrical communication with target tissue, such as first and second target tissues, respectively, associated with direct or indirect control of a posterior base of the tongue and posterior oropharyngeal airway of the subject. A sensor signal can then be generated by the sensing component based on a detected at least one physiological parameter or a related symptom associated with OSA. The controller can activate the neuromuscular stimulator to adjust application of the therapy signal to the first target tissue in response to the sensor signal to treat the OSA.

Another aspect of the present disclosure relates to a method for treating a sleep breathing disorder in a subject suffering therefrom. One step of such a method includes obtaining a neurostimulator having at least one lead and further comprising an electrode and a sensing component. Both the electrode and the sensing component can be located on the at least one lead. The method can also include placing at least a portion of the neurostimulator on or in the subject's mandible. Next, the neurostimulator can be positioned so that the electrode and the sensing component are in electrical communication with a muscle that controls an upper airway of the subject. The method can further include generating a sensor signal, by the sensing component, based on a detected activity of the muscle that is a biomarker of respiration. The neurostimulator can be activated to deliver an electrical signal to the muscle in response to the sensor signal to open the subject's upper airway. The electrical signal can be delivered in sync with any phase of respiration, including inhalation or exhalation.

Another aspect of the present disclosure relates to a method for treating disordered breathing that occurs during sleep in a subject. The method includes obtaining a neurostimulator comprising a lead having an electrode located thereon and positioning the neurostimulator so that the electrode and an electromyogram (EMG) sensor are in electrical communication with a muscle or nerve that controls an upper airway of the subject. The method further includes monitoring the subject for an EMG signal indicative of a certain period of a respiratory cycle of the subject and by sensing EMG activity of the muscle and activating the neurostimulator to provide an electrical signal to the muscle or nerve in response to the EMG signal to decrease the subject's airway resistance and treat the sleep disordered breathing.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 6A is a frontal view of a human skull and mandible with the chin implant of FIG. 4 correctly positioned;

FIG. 6B is a profile view of the skull depicted in FIG. 6A;

FIG. 12 is a process flow diagram illustrating a method for treating a sleep breathing disorder according to another aspect of the present disclosure.

DETAILED DESCRIPTION

Definitions

Figure 1:
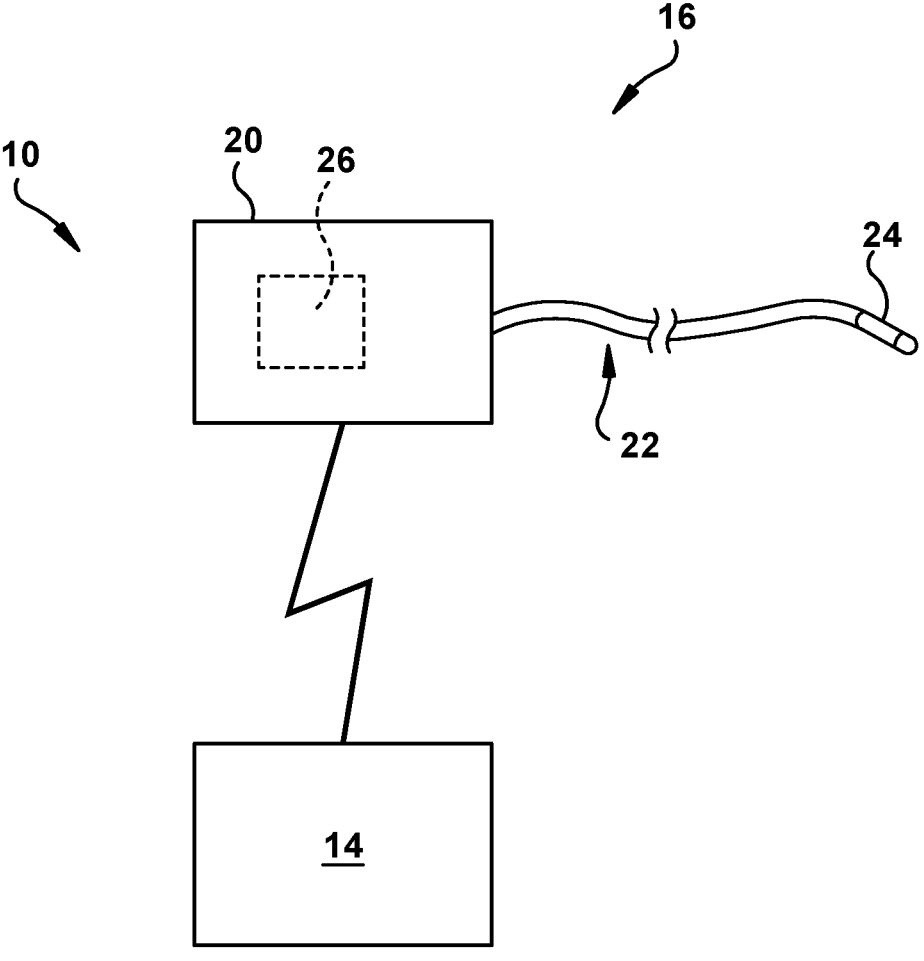
FIG. 1 is a schematic illustration of a system for treating obstructive sleep apnea (OSA) constructed in accordance with one aspect of the present disclosure.

Unless defined otherwise, all technical and scientific terms used herein have the same meaning as is commonly understood by one of skill in the art to which the present disclosure pertains.

In the context of the present disclosure, the terms "modulate" or "modulating" can refer to causing a change in neuronal and/or muscle activity, chemistry, and/or metabolism. The change can refer to an increase, decrease, or even a change in a pattern of neuronal and/or muscle activity. The terms may refer to either excitatory or inhibitory stimulation, or a combination thereof, and may be at least electrical, magnetic, optical or chemical, or a combination of two or more of these.

As used herein, the term "electrically stimulate" or "electrical stimulation" refers to either excitatory or inhibitory stimulation or a combination thereof.

As used herein, the term "electrical communication" can refer to the ability of an electric field generated by an electrode or electrode array to be transferred, or to have a neuromodulatory effect, within and/or on a target tissue, such as a muscle or nerve.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "obstructive sleep apnea" or "OSA" can refer to a breathing disorder that occurs primarily during sleep with consequences that may persist throughout the waking hours in the form of sleepiness. OSA can be characterized by periodic collapse of the upper airway during sleep with apneas, hypopneas, or a continuous or sustained reduction in ventilation and excessive daytime sleepiness, neurocognitive defects and depression.

As used herein, the term "treating" can refer to therapeutically regulating, preventing, improving, alleviating the signs and symptoms of, and/or reducing the effects of a sleeping disorder, such as OSA and oropharyngeal airway obstruction. The term can also refer to chronic or acute treatment.

As used herein, the term "therapy signal" can refer to an electrical and/or chemical signal that is delivered to a target tissue and is capable of modulating (e.g., electrically modulating) the target tissue and/or a bodily organ (e.g., a tongue) associated with the target tissue.

When an element or structure is referred to herein as being "on," "engaged to," "connected to," "attached to", or "coupled to" another element or structure, it may be directly on, engaged, connected or coupled to the other element or structure, or intervening elements or structures may be present. In contrast, when an element is referred to as being "directly on," "directly engaged to," "directly connected to," or "directly coupled to" another element or structure, there may be no intervening elements or structures present. Other words used to describe the relationship between elements should be interpreted in a like fashion (e.g., "between" versus "directly between," "adjacent" versus "directly adjacent," etc.).

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated.

Overview

The present disclosure relates generally to a system and method for treating sleep disorders and, more particularly, to a system and method for treating OSA. As shown in FIG. 1, one aspect of the present disclosure can include a system 10 for treating a sleeping disorder, such as OSA. OSA affects almost every system in the body and, in some individuals, can result in increased incidence of cardiovascular disease. As discussed in more detail below, the present disclosure provides a minimally invasive, implantable system 10 configured to modulate one or more muscles of the anterior lingual musculature 12 (FIG. 8) and thereby open airflow and prevent or mitigate obstruction during sleep. Advantageously, the present disclosure helps to minimize the deleterious effects of OSA on the day-to-day life of individuals suffering from OSA, as well as preventing or mitigating stress on certain muscles that are being unnecessarily stimulated as a result of other treatment for OSA. Such advantages are realized, at least in part, because: (1) only a single surgical site is required for implantation of the system 10; (2) the system can be configured for highly selective stimulation of one or more muscles comprising the anterior lingual musculature; (3) dissection of the hypoglossal nerve trunk is not required to practice the present disclosure; (4) implantation of the system does not produce any visible scarring; and (5) once implanted, subjects cannot see, feel, or sense the presence of the system.

System

In one aspect, the present disclosure can include a system 10 (FIG. 1) for treating OSA in a subject. The system 10 can comprise a power source 14 in electrical communication with a neuromuscular stimulator 16. The power source 14 and the neuromuscular stimulator 16 can be in direct and/or indirect electrical communication with one another. In some instances, the power source 14 and the neuromuscular stimulator 16 can be in direct electrical communication with one another via one or more wires (not shown). In other instances, the power source 14 and the neuromuscular stimulator 16 can be in indirect electrical communication with one another (e.g., via a wireless link). The system 10 can be portable and adapted to be borne by a subject suffering from OSA for a desired period of time. In some instances, the system 10 can be borne by a subject for an acute period of time (e.g., during an emergency situation), for a semi-chronic period of time (e.g., less than about a week to about 6 weeks), or for a chronic period of time (e.g., greater than about 6 weeks). For example, the neuromuscular stimulator 16 can be temporarily or permanently implanted within, on, or otherwise associated with a subject suffering from OSA.

In another aspect, the power source 14 can be configured to deliver a therapy signal having certain power and stimulation parameters to the neuromuscular stimulator 16. Examples of such power and stimulation parameters can include the pulse waveform, the signal pulse width, the signal pulse frequency, the signal pulse phase, the signal pulse polarity, the signal pulse amplitude, the signal pulse intensity, and the signal pulse duration of the therapy signal. The power source 14 can be capable of conveying a variety of currents and voltages to the neuromuscular stimulator 16. In some instances, the power source 14 can communicate stimulating energy, such as electrical current pulses to the neuromuscular stimulator. The power source 14 can optionally include circuitry and/or other implantable components for outputting electrical pulses to the neuromuscular stimulator 16. Signals from the power source 14 can additionally or optionally be communicative in nature, for example, communicating stimulation program information, subject information, and other types of information. In some instances, the power source 14 is located external to the subject and in electrical communication with the neuromuscular stimulator 16 via inductive coupling. For example, the power source 14 can be configured as part of a wearable device, such as a chin strap 18 (FIG. 2), which may be worn at bedtime. In such instances, the power source 14 is not physically "wired" to the neuromuscular stimulator 16 (FIG. 1).

In another aspect, the neuromuscular stimulator 16 can include any active implantable medical device configured for implantation for a relatively short or long period of time. As shown in FIG. 1, the neuromuscular stimulator 16 can include a housing 20 connected to one or more electrical leads 22 having at least one electrode 24 associated there-with. Various electrical components, such as a controller 26, can be hermetically sealed and contained within the housing 20. As discussed in more detail below, all or only a portion of the neuromuscular stimulator 16 can be configured for implantation on or in the mandible of a subject. For example, all or only a portion of the neuromuscular stimulator 16 can be configured for implantation on, in, or through a mandible 28 (e.g., the mentum 29) (FIG. 8) of the subject.

The controller 26 (FIG. 1) can be configured to receive the power and stimulation parameters associated with a therapy signal from the power source 14. In some instances, the controller 26 can include a microprocessor (not shown), a hardwired circuit (not shown), or other appropriate means for controlling various aspects of the system 10. For example, the controller 26 can operate the power source 14, convey therapy signals to the at least one electrode 24, and/or receive information from various sources, such as the at least one electrode or a sensor (not shown). The controller 26 can be configured to store a stimulation program (or programs) and operate the power source 14 according to the stimulation program(s). Stimulation programs can include predetermined, set programs (e.g., hardwired into the controller) and adaptive, dynamic programs (e.g., software that adapts an artificial stimulation pattern according to various inputs). The controller 26 can select between various programs and/or actively modify a stimulation program according to various inputs, such as information received from a subject, information received from a sensor, information received from the power source 14, information received from the at least one electrode 24, and/or information received from a health care provider.

In another aspect, the lead 22 of the neuromuscular stimulator 16 can include at least one electrode 24 that is in electrical communication with the controller 26. The at least one electrode 24 can be configured to deliver a therapy signal to a target tissue associated with direct or indirect control of a posterior base of the tongue of a subject. In further describing representative electrodes 24, which are described in the singular, it will be apparent that more than one electrode may be used as part of the system 10. Accordingly, the description of a representative electrode 24 suitable for use in the system 10 of the present disclosure is applicable to other electrodes that may be employed.

The electrode 24 can include one or more of the following types and/or categories of electrodes: epimysial electrodes; intramuscular electrodes, such as Peterson electrodes; nerve cuff electrodes; self-contained electrodes; monopolar electrodes; bipolar electrodes; multi-contact electrodes; and/or other known electrode types/categories and combinations thereof. It will be appreciated that the electrode 24 can include one or more associated flexible, extensible electrical leads 22. The lead 22 and/or the electrode 24 can be highly flexible so as to not hinder regular tongue movement. In some instances, all or only a portion of the lead 22 can include one or more deployable anchoring elements (not shown) (e.g., barbs, hooks, etc.). The anchoring element(s) can be selectively retractable and extendable. The anchoring element(s) facilitate secure placement of the lead 22 (and thus the electrode 24) in or about a target tissue, such as a muscle, which is under constant flexion and relaxation.

The electrode 24 can be controllable to provide therapy signals that may be varied in voltage, frequency, pulse-width, current and/or intensity. For example, the electrode 24 can also provide both positive and negative current flow from the electrode and/or be capable of stopping current flow from the electrode and/or changing the direction of current flow from the electrode. In some instances, the electrode 24 has the capacity for variable output, linear output and short pulse-width. In other instances, the electrode 24 can comprise a coil configured to deliver magnetic stimulation. The electrode 24 may be mono-polar, bipolar or multi-polar. To minimize the risk of an immune response triggered by the subject against certain components of the neuromuscular stimulator 16, and also to minimize damage thereto (e.g., corrosion from other biological fluids, etc.), the electrode 24 (and any wires and optional housing materials) can be made of inert materials, such as silicon, metal, plastic and the like. In other instances, the electrode 24 can be a multi-vector electrode capable of directing current to different muscles of anterior lingual musculature 12. In further instances, the system 10 can include more than one electrode 24, such as an array of electrodes to stimulate a field of aborizing hypoglossal branches associated with a particular target muscle (or group of muscles).

In another aspect, the system 10 can be configured as an open-loop or closed-loop system. In an open-loop system, for example, a physician or the subject may, at any time, manually by the use of a remote controller adjust treatment parameters of the system 10. Alternatively, in a closed-loop system (discussed below), treatment parameters (e.g., electrical signals) may be automatically adjusted in response to a sensed physiological parameter or a related symptom indicative of the extent of OSA. In a closed-loop feedback system, a sensor that senses a physiological parameter associated with OSA (e.g., muscle and/or nerve electrical activity, tongue position, oropharyngeal airflow, etc.) can be utilized. More detailed descriptions of sensors that may be employed in a closed-loop system, as well as other examples of sensors and feedback control techniques that may be employed as part of the present disclosure are disclosed in U.S. Pat. No. 5,716,377.

Closed-Loop System

In another aspect, the present disclosure can include a closed-loop system 50 (FIG. 3) for treating OSA in a subject. The system 50 can comprise a power source 14, a neuromuscular stimulator 16, and a controller 26. The power source 14 and the neuromuscular stimulator 16 can be in direct and/or indirect electrical communication with one another. In some instances, the power source 14 and the neuromuscular stimulator 16 can be in direct electrical communication with one another via one or more wires (not shown). In other instances, the power source 14 and the neuromuscular stimulator 16 can be in indirect electrical communication with one another (e.g., via a wireless link). One or more components of the system 50 can be implantable in a subject suffering from OSA for a desired period of time (e.g., acute, semi-chronic, chronic). The system 50 can also be portable and adapted to be borne by a subject suffering from OSA for a desired period of time. In some instances, the system 50 can be borne by a subject for an acute period of time (e.g., during an emergency situation), for a semi-chronic period of time (e.g., less than about a week to about 6 weeks), or for a chronic period of time (e.g., greater than about 6 weeks). For example, the neuromuscular stimulator 16 can be temporarily or permanently implanted within, on, or otherwise associated with a subject suffering from OSA.

In another aspect, the power source 14 can be configured to deliver a therapy signal having certain power and stimulation parameters to the neuromuscular stimulator 16. Examples of such power and stimulation parameters can include the pulse waveform, the signal pulse width, the signal pulse frequency, the signal pulse phase, the signal pulse polarity, the signal pulse amplitude, the signal pulse intensity, and the signal pulse duration of the therapy signal. The power source 14 can be capable of conveying a variety of currents and voltages to the neuromuscular stimulator 16. In some instances, the power source 14 can communicate stimulating energy, such as electrical current pulses to the neuromuscular stimulator. The power source 14 can optionally include circuitry and/or other implantable components for outputting electrical pulses to the neuromuscular stimulator 16. Signals from the power source 14 can additionally or optionally be communicative in nature, for example, communicating stimulation program information, subject information, and other types of information. In some instances, the power source 14 is located external to the subject and in electrical communication with the neuromuscular stimulator 16 via inductive coupling. For example, the power source 14 can be configured as part of a wearable device, such as a chin strap (not shown), which may be worn at bedtime. In such instances, the power source 14 is not physically "wired" to the neuromuscular stimulator 16.

In another aspect, the neuromuscular stimulator 16 can include any active implantable medical device configured for implantation for a relatively short or long period of time. As discussed in more detail below, all or only a portion of the neuromuscular stimulator 16 can be configured for implantation on or in the mandible of a subject. For example, all or only a portion of the neuromuscular stimulator 16 can be configured for implantation on, in, or through a mandible 28 (e.g., the mentum 29) of the subject.

The controller 26 can be configured to receive the power and stimulation parameters associated with a therapy signal from the power source 14. In some instances, the controller 26 can include a microprocessor (not shown), a hardwired circuit (not shown), or other appropriate means for controlling various aspects of the system 50. For example, the controller 26 can operate the power source 14, convey therapy signals to at least one electrode 24, and/or receive information from various sources, such as the electrode or a sensing component 52. The controller 26 can be configured to store a stimulation program (or programs) and operate the power source 14 according to the stimulation program(s). Stimulation programs can include predetermined, set programs (e.g., hardwired into the controller) and adaptive, dynamic programs (e.g., software that adapts an artificial stimulation pattern according to various inputs). The controller 26 can select between various programs and/or actively modify a stimulation program according to various inputs, such as information received from a subject, information received from the sensing component 52, information received from the power source 14, information received from the at least one electrode 24, and/or information received from a health care provider.

In another aspect, the neuromuscular stimulator 16 can include one or more leads 22 (FIG. 4), each of which has at least one electrode 24 in electrical communication with the controller 26. The at least one electrode 24 can be configured to deliver a therapy signal to a target tissue associated with direct or indirect control of a posterior base of the tongue of a subject. In further describing representative electrodes 24, which are described in the singular, it will be apparent that more than one electrode may be used as part of the system 50. Accordingly, the description of a representative electrode 24 suitable for use in the system 50 of the present disclosure is applicable to other electrodes that may be employed.

The electrode 24 can include one or more of the following types and/or categories of electrodes: epimysial electrodes; intramuscular electrodes, such as Peterson electrodes; nerve cuff electrodes; self-contained electrodes; monopolar electrodes; bipolar electrodes; multi-contact electrodes; and/or other known electrode types/categories and combinations thereof. It will be appreciated that the electrode 18 can include one or more associated flexible, extensible electrical leads 22. The lead 22 and/or the electrode 24 can be highly flexible so as to not hinder regular tongue movement. In some instances, all or only a portion of the lead 22 can include one or more deployable anchoring elements (not shown) (e.g., barbs, hooks, etc.). The anchoring element(s) can be selectively retractable and extendable. The anchoring element(s) facilitate secure placement of the lead 22 (and thus the electrode 24) in or about a target tissue, such as a muscle, which is under constant flexion and relaxation.

The electrode 24 can be controllable to provide therapy signals that may be varied in voltage, frequency, pulse-width, current and/or intensity. For example, the electrode 24 can also provide both positive and negative current flow from the electrode and/or be capable of stopping current flow from the electrode and/or changing the direction of current flow from the electrode. In some instances, the electrode 24 has the capacity for variable output, linear output and short pulse-width. In other instances, the electrode 24 can comprise a coil configured to deliver magnetic stimulation. The electrode 24 may be mono-polar, bipolar or multi-polar. To minimize the risk of an immune response triggered by the subject against certain components of the neuromuscular stimulator 16, and also to minimize damage thereto (e.g., corrosion from other biological fluids, etc.), the electrode 24 (and any wires and optional housing materials) can be made of inert materials, such as silicon, metal, plastic and the like. In other instances, the electrode 24 can be a multi-vector electrode capable of directing current to different muscles of anterior lingual musculature. In further instances, the system 50 can include more than one electrode 24, such as an array of electrodes to stimulate a field of arborizing hypoglossal branches associated with a particular target muscle (or group of muscles including bilateral stimulation of arborizing branches).

In another aspect, the system 50 also includes one or more sensing components 52 configured to detect at least one physiological parameter or a related symptom of OSA. The presence of the sensing component 52 enables closed-loop operation of the system 50 to treat OSA, meaning that treatment parameters (e.g., therapy signals) may be automatically adjusted in response to the sensed or detected physiological parameter or a related symptom of OSA. In some instances, the sensing component 52 and the electrode 24 can be the same structure or element. Advantageously, use of a single structure or element as the sensing component 52 and the electrode 24 reduces the invasive nature of the surgical procedure associated with implanting the system 50, while also reducing the number of foreign bodies introduced into a subject.

The sensing component 52 can be in direct and/or indirect electrical communication with the controller 26 and/or the power source 14 (e.g., via one or more leads 22 or a wireless link). In one example, the sensing component 52 can comprise a sensor (e.g., an electrode 24 as described above) that senses a physiological parameter or related symptom associated with OSA (e.g., muscle and/or nerve electrical activity, tongue position, oropharyngeal airflow, etc.). Examples of sensors that may be employed in a closed-loop system 50, as well as other examples of sensors and feedback control techniques that may be employed as part of the present disclosure are disclosed in U.S. Pat. No. 5,716,377.

The system 50 can be configured for highly selective stimulation and modulation of the anterior lingual musculature. In some instances, the system 50 can comprise multiple leads 22, each of which includes at least one electrode 24 and at least one sensing component 52. For example, the system 50 can have an "octopus-like" configuration whereby the tentacles correspond to the multiple leads 22 and the body corresponds to the neuromuscular stimulator 16. A distal end of each of the leads 22 can be configured for embedding into a pre-determined portion of a muscle comprising the anterior lingual musculature. The muscle(s) in which the distal ends of the leads 22 is/are embedded can be the same or different. Thus, in some instances, the distal ends of the leads 22 can be embedded in a single muscle but at different spatial locations. In such instances, the system 50 can be operated to activate (stimulate) a first portion of the muscle associated with a first lead (not shown), while simultaneously or sequentially inhibiting muscle function in a second different portion of the muscle associated with a second lead (not shown). Advantageously, a system 50 having a multiple-lead configuration provides highly selective control over targeted muscles of the anterior lingual musculature and, thus, the ability to therapeutically modulate the laryngeal introitus.

One example of a system 50 for treating OSA is illustrated in FIGS. 4-6B. The system 50 can comprise a chin implant 54 for a human mandible 28 (FIGS. 6A-B). The chin implant 54 (FIG. 4) has a generally crescent-shaped configuration and, when implanted, gives the appearance of a natural chin contour. All or only a portion of the chin implant 54 can be made of one or more materials that is/are biologically inert and non-reactive to avoid infection in a subject's body (e.g., silicone and/or or plastic). By virtue of its construction, the chin implant 54 can be pliant, flexible and compressible.

Figure 4:
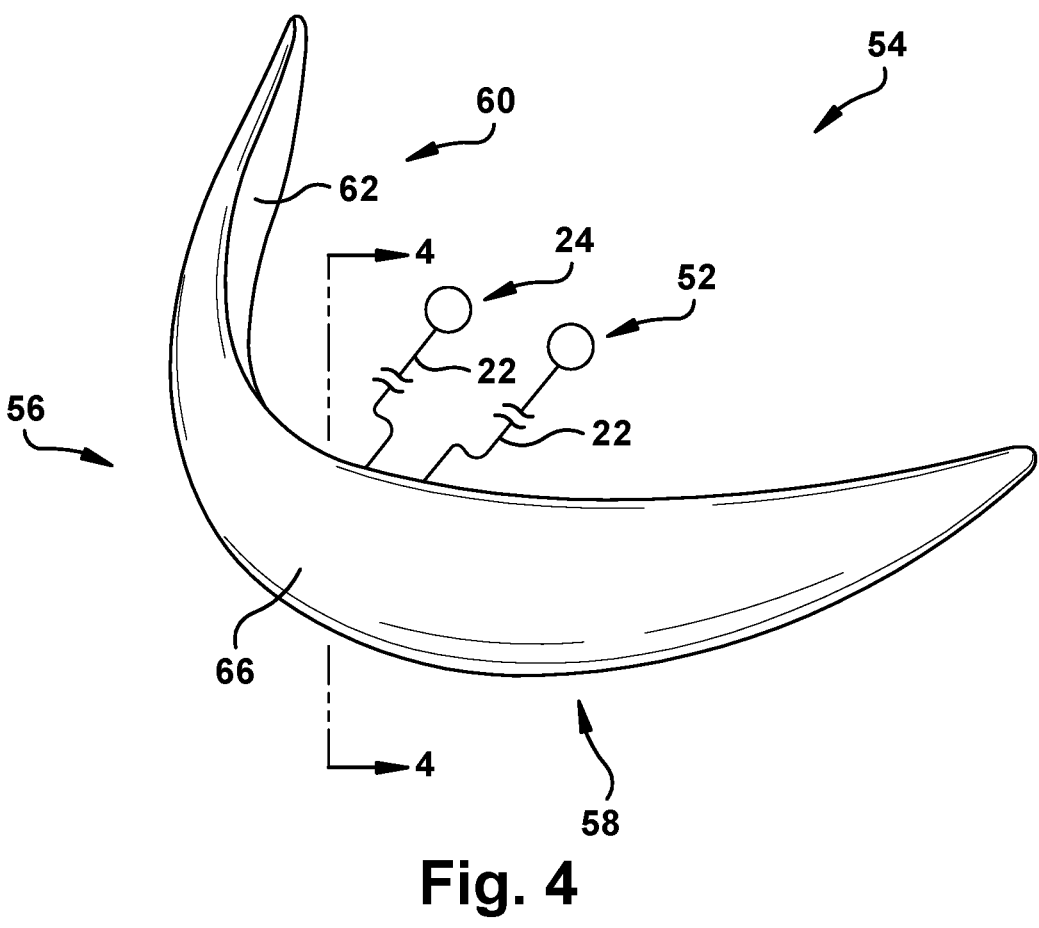
FIG. 4 is a perspective view of a system for treating OSA configured as a chin implant.
Figure 5:
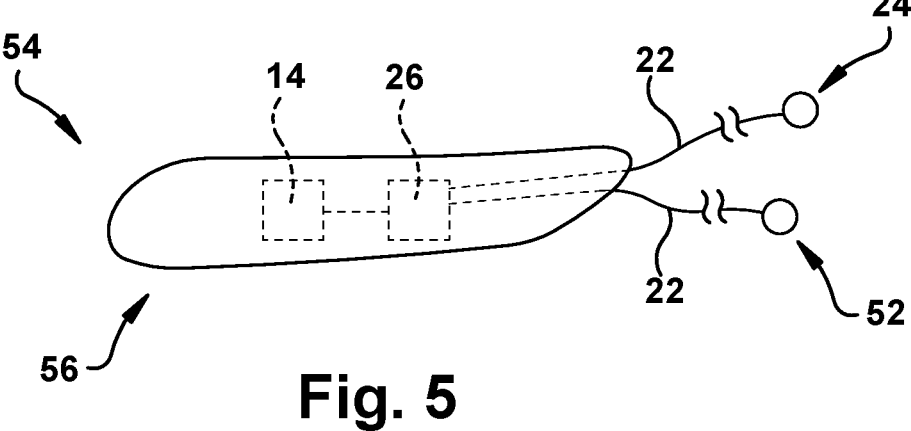
FIG. 5 is a cross-sectional view taken along Line 4-4 of the chin implant in FIG. 4.
Figures 6C, 6D:
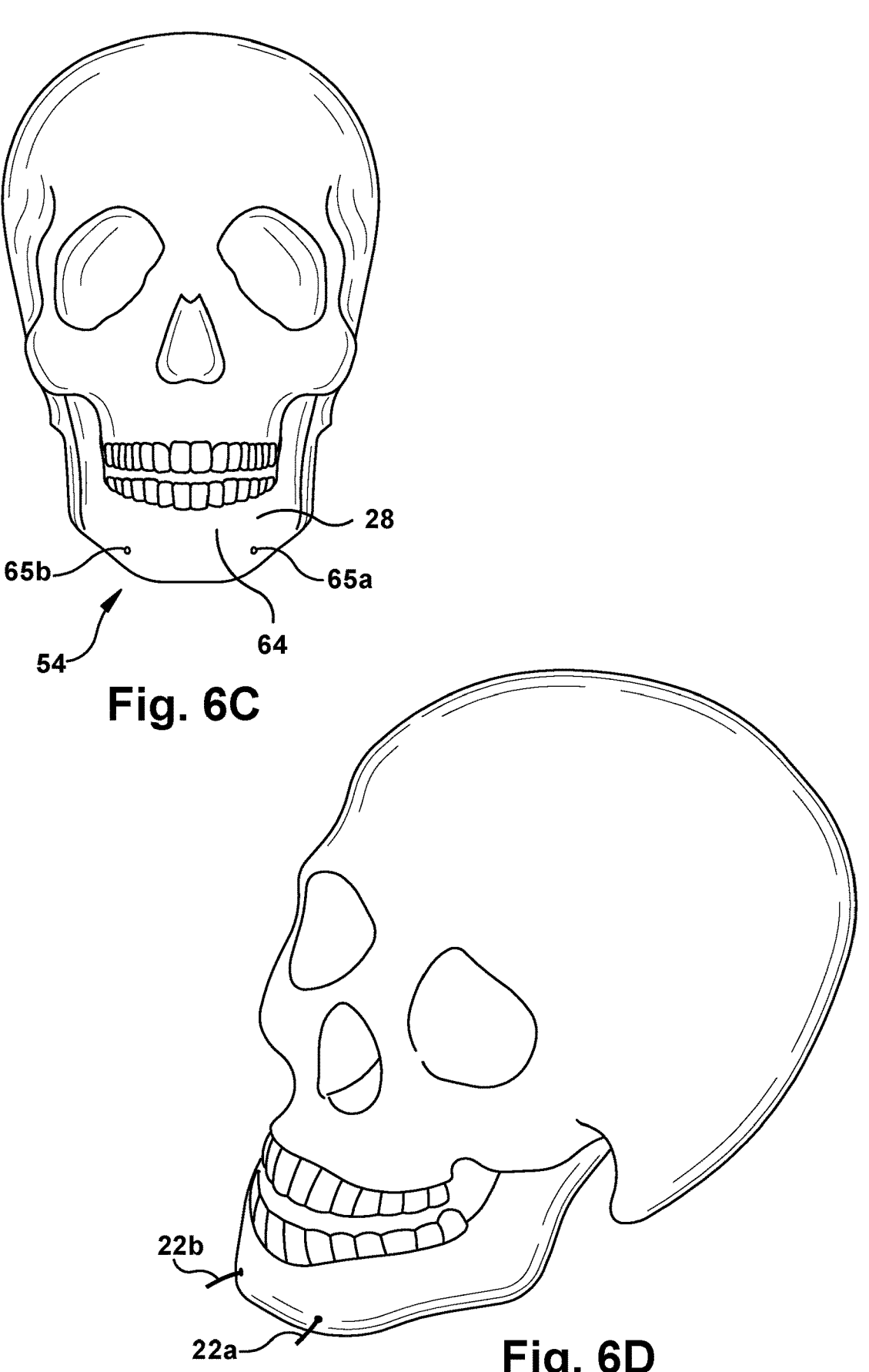
FIG. 6C is a frontal view of a human skull and mandible illustrating holes drilled through the mandible.
FIG. 6D is a perspective view of a human skull illustrating leads inserted through the drill holes of FIG. 6C.

As shown in FIGS. 4-5, the chin implant 54 can comprise an implant body 56, a controller 26, at least one electrode 24, a sensing component 52, and a power source 14. The implant body 56 can have a front face 58 and a back face 60. The back face 60 can have a surface 62 for placement adjacent the mental protuberance 64 of the mandible 28 (FIG. 6A). The front face 58 can have a curved projection surface 66 for protruding from the chin to create a natural chin profile after implantation (FIG. 6B). Each of the controller 26, the at least one electrode 24, the sensing component 52, and the power source 14 can be directly or indirectly associated with the implant body 56. As shown in FIG. 4, for example, the controller 26 and the power source 14 can be housed within a portion of the implant body 56, while the at least one electrode 24 and the sensing component 52 are located external to the implant body and directly connected to the controller (e.g., by leads 22). Although the power source 14 is shown as being disposed within the implant body 56, it will be appreciated that the power source may also be located external to the implant body (e.g., via a wireless link).

Methods

Figure 7:
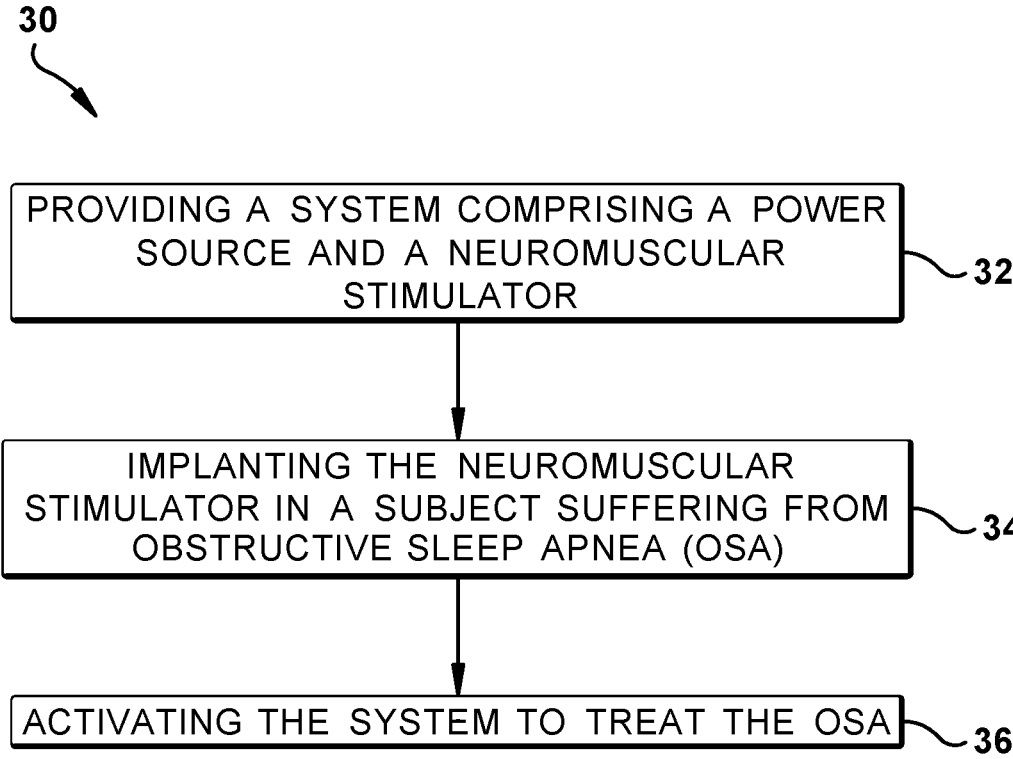
FIG. 7 is a process flow diagram illustrating a method for treating OSA according to another aspect of the present disclosure.

Another aspect of the present disclosure can include a method 30 (FIG. 7) for treating OSA in a subject. The method 30 can generally include the steps of providing a system 10 (Step 32), implanting a neuromuscular stimulator 16 of the system into a subject suffering from OSA (Step 34), and activating the system to treat the OSA (Step 36). The system 10 provided at Step 32 can be identically or similarly constructed as the system shown in FIG. 1 and described above. For the purpose of illustration only, the method 30 will be described below using the system 10 shown in FIG. 1.

At Step 34, the neuromuscular stimulator 16 can be implanted in the subject. In some instances, a trans-mandibular surgical approach can be used to implant the neuromuscular stimulator 16. A variety of trans-mandibular surgical approach options may be used, such as a submental approach or an intraoral bucca-gingival sulcus approach. Generally speaking, a submental approach allows for other adjunctive procedures including, but not limited to, cervical liposuction (e.g., for effacement of platysmal banding), elevation of hyoid positioning, and mandibular distal bone advancement for aesthetic purposes and/or functionally repositioning the anterior lingual musculature 12. Unlike the submental approach, an intraoral approach does not produce a facial scar. A trans-mandibular surgical approach can be performed under local anesthetic or in an outpatient setting; however, it will be appreciated that general anesthetic may alternatively be used as patients may be more comfortable and the patient's airway is better protected.

Figure 8:
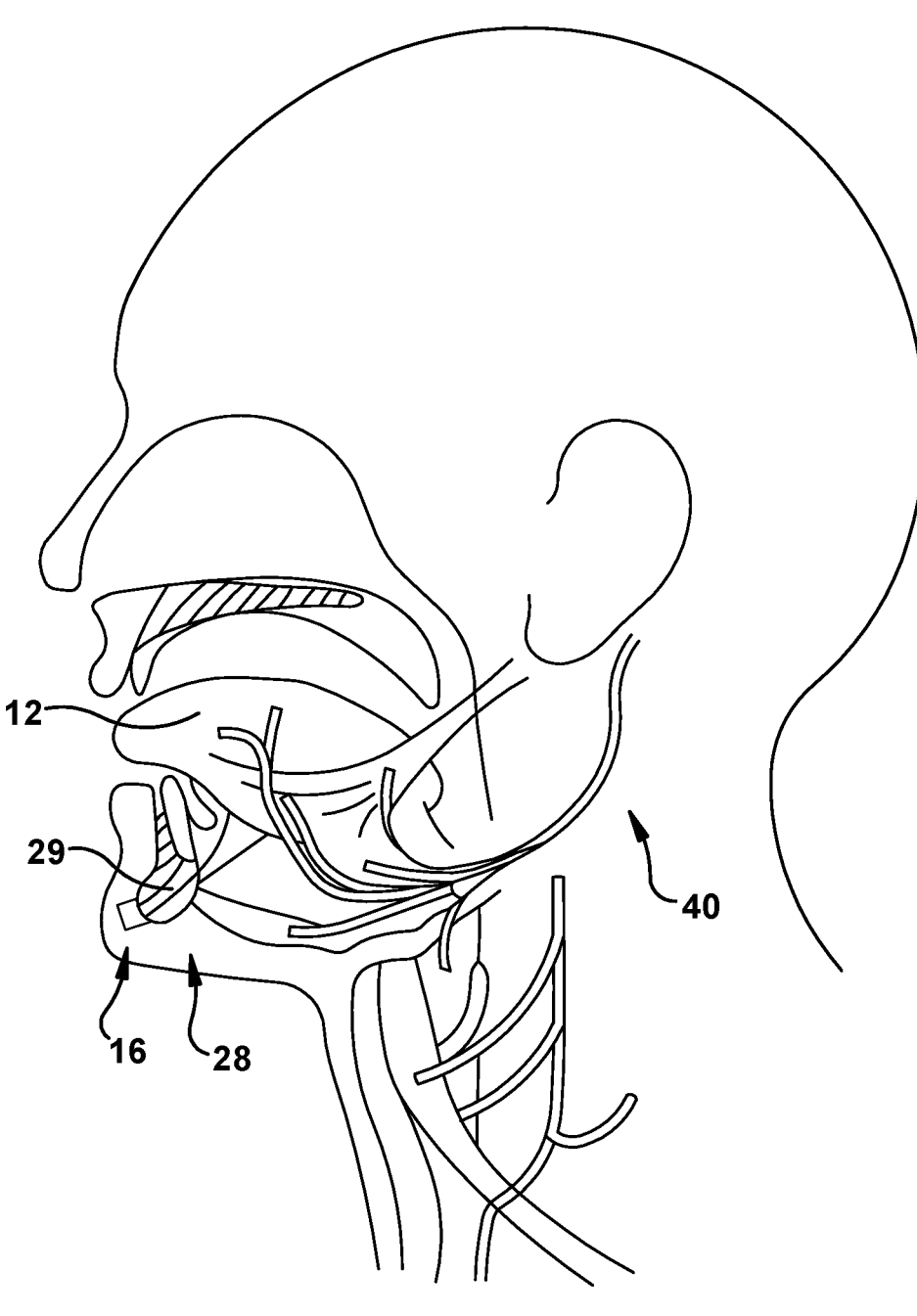
FIG. 8 is a schematic illustration showing the neuromuscular stimulator in FIG. 1 implanted in a subject.

Whether a submental or intraoral bucca-gingival sulcus approach is used, the dissection can be carried out to the level of the periosteum overlying the mentum 29 of the mandible 28 (FIG. 8). Surgical awareness is highlighted at this time in an effort to preserve and not traumatize the mental nerves (not shown). The mental nerves exit at the mid-vertical level of the mandible 28, between the region of the first and second pre-molars bilaterally. Like many surgeries in the head and neck, preservation of a nerve (or nerves) along with strict attention to hemostasis are key features of a successful operation. In making the gingivo-labial sulcus incision, for example, it can be important to leave an adequate cuff of mucosa along with a sufficient portion of the mentalis muscle (not shown) for later resuspension. Doing so can avoid lower-lip ptosis.

Figure 9A:
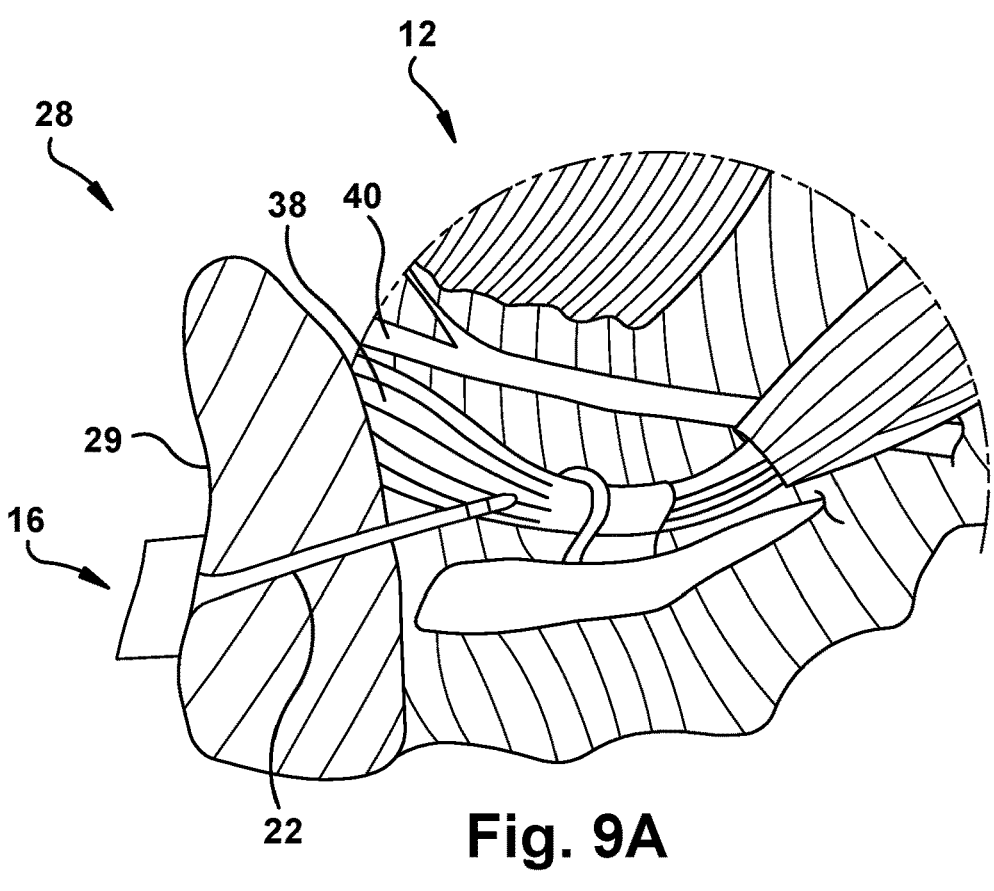
FIG. 9A is a schematic illustration showing a magnified view of the neuromuscular stimulator in FIG. 8.
Figure 9B:
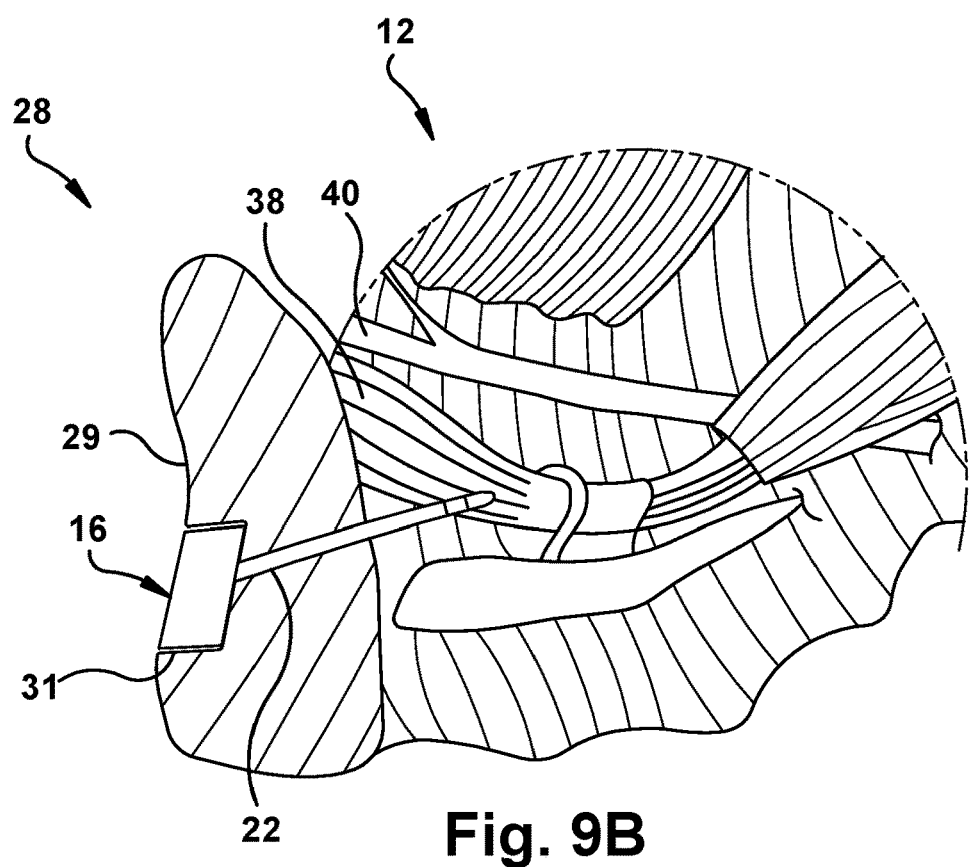
FIG. 9B is a schematic illustration showing the neuromuscular stimulator of FIG. 1 placed within a sulcus of an anterior mandible of a human skull.
Figure 10:
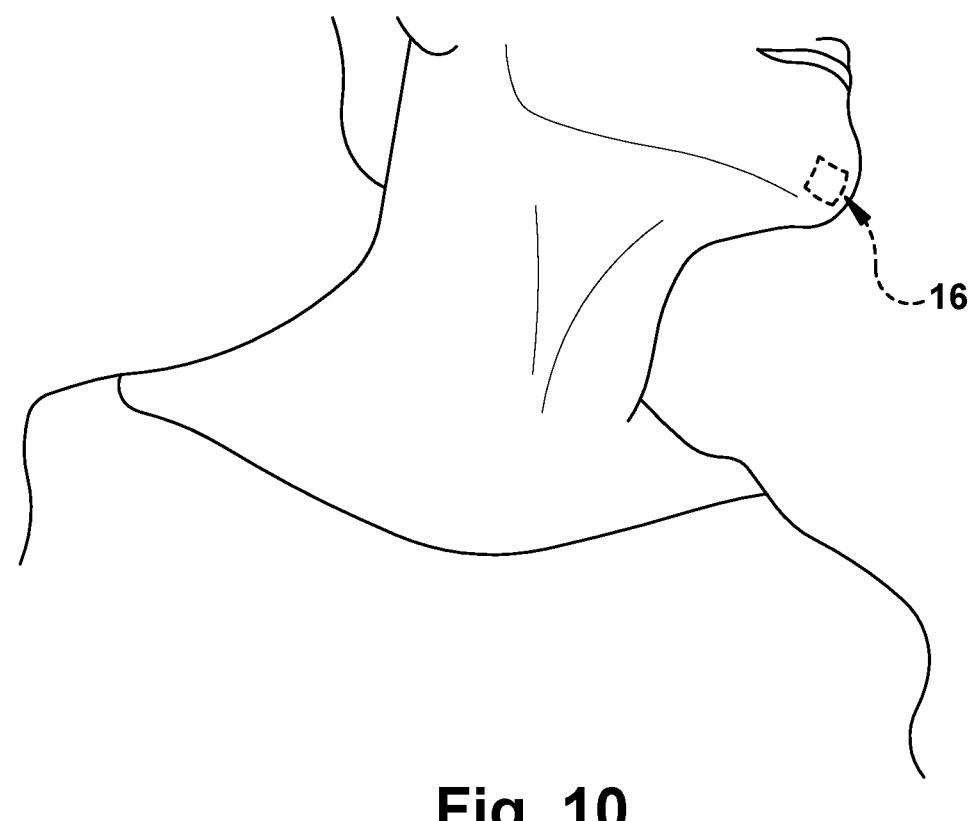
FIG. 10 is a schematic illustration showing the neuromuscular stimulator in FIG. 9 implanted in the subject.

FIGS. 8-10 illustrate a submental approach for implanting the neuromuscular stimulator 16 in a subject. First, an external submental crease incision (not shown) can be made. A subperiosteal dissection can then be made to elevate the periosteum and protect the mental nerves. At this point, a surgical mark can be made at the midline of the bony mentum 29. One or more drill holes (65a and 65b illustrated in FIG. 6C) can be made above the inferior edge of the mentum 29, and on either side of the midline. For example, multiple drill holes can be made about 1 cm above the inferior edge of the mentum 29, and about 1.5 cm on either side of the midline. The diameter of each drill hole should be sufficient to pass the lead(s) (22a and 22b illustrated in FIG. 6D) of the neuromuscular stimulator 16 through both cortices of the mandible 28 into electrical communication with one or more of the sublingual muscles that control the anterior positioning of the tongue base when contraction occurs.

In another example, an intraoral bucca-gingival sulcus approach can alternatively be used to implant the neuromuscular stimulator 16. Subperiosteal dissection can be carried out laterally to identify the mental nerves. The foramina (not shown) of the mental nerves are generally found between the first and second premolar teeth at the level of the origin of the mentalis muscle, or 2-4 mm below the level of the bicuspid premolar teeth apices. The foramina are situated deep to the midportion of the depressor anguli oris. Dissection can occur inferolaterally to allow for a longer osteotomy and thereby prevent unsightly mandibular notching. During dissection, the periosteum at the inferior rim of the mentum 29 can be left intact. Next, the skeletal midline can be aligned with the overlying soft tissue corollary. A sagittal saw with a 30-degree bend can then be used to facilitate an even cut while minimizing soft tissue trauma. Lateral cuts can be made about 4-5 mm below the foramina to compensate for the path of the inferior alveolar nerve.

In another variation of the method 30, the neuromuscular stimulator 16 can be configured to also serve as a chin implant. This may be desirable in instances where a subject desires an aesthetic change to their anterior mandibular profile. Alternatively, if a subject does not desire a change in their anterior mandibular profile, a relatively small or low-profile neuromuscular stimulator 16 that does not cause any profile changes can be used. For example, a neuromuscular stimulator 16 can be sized and dimensioned for placement within a drilled sulcus (31 illustrated in FIG. 9B) such that attachment of the neuromuscular stimulator therein does not interfere with the anterior mandibular profile of the subject.

Regardless of the trans-mandibular surgical approach used, the neuromuscular stimulator 16 can be implanted so that the electrode 24 is in electrical communication with a target tissue associated with control of a posterior base of the tongue of the subject (e.g., the electrode can be placed directly on and/or within the target tissue). In some instances, the electrode 24 can be placed into electrical communication with one or more muscles of the anterior lingual musculature 12. In other instances, two or more electrodes 24 can be placed bilaterally into electrical communication with one or more muscles of the anterior lingual musculature 12. In one example, the electrode 24 can be placed into electrical communication with a genioglossus muscle (not shown). In another example, the electrode 24 can be placed into electrical communication with an anterior belly digastric muscle 38 (FIG. 9). In another example, the electrode 24 can be placed into electrical communication with a hyoglossus muscle (not shown). In another example, the electrode 24 can be placed into electrical communication with a mylohyoid muscle (not shown).

Alternatively or additionally, the electrode 24 can be placed into electrical communication with a nerve (or nerves) that innervates one or muscles associated with control of a posterior base of the tongue of the subject, such as the hypoglossal nerve 40 and/or its distal arborizing branches at or near its neuromuscular junction. In some instances, the electrode 24 can be implanted directly in or on the target tissue. In other instances, the electrode can be implanted so that the electrode 24 is not in direct physical contact with the target tissue, but located in sufficient proximity to the target tissue such that delivery of a therapy signal to the electrode can modulate target tissue activity.

Proper positioning of the lead 22 can be confirmed by delivering test signals to the electrode 24 and then noting if the test signals result in anterior displacement of the posterior base of the tongue. Once the lead 22 is properly positioned, the housing 20 can be securely affixed to the subject. For example, the housing 20 can be securely affixed (e.g., with bone screws) into the external cortex of the mandible 28, or simply placed in a tight surgical subperiosteal pocket. Once the neuromuscular stimulator 16 is secured to the subject, the soft tissue can be closed in layers while paying special attention to the reattachment of the mentalis muscle to avoid ptotic lower lip. The soft tissue can then be re-draped with tape and the procedure completed (FIG. 10). Overall, the surgical implant procedure can take about 15 minutes to complete.

Figure 2:
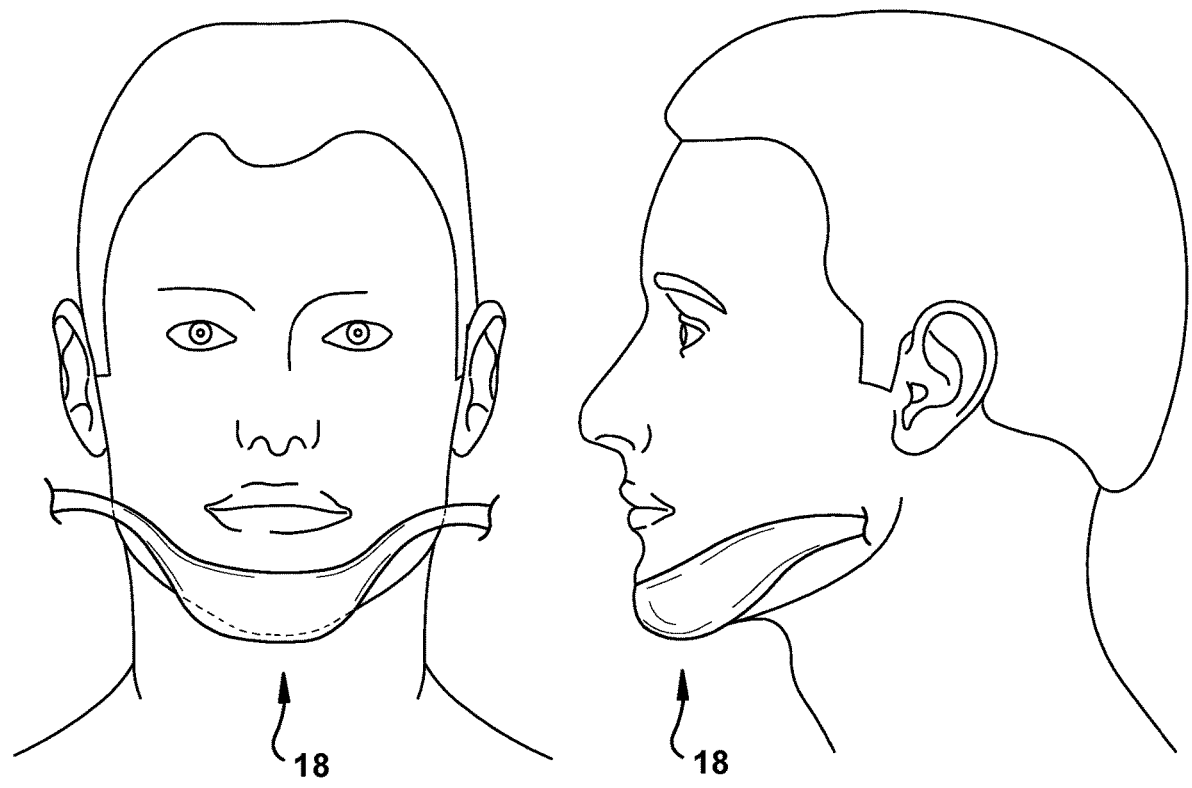
FIG. 2 is a schematic illustration showing a power source of the system in FIG. 1 configured as a chin strap.

At Step 34, the power source 14 can be associated with the subject (if it has not been done so already) so that the power source is in electrical communication with the neuromuscular stimulator 16. As shown in FIG. 2 and discussed above, for example, the power source 14 can be configured as a chin strap 18 and placed around the head of the subject.

With the neuromuscular stimulator 16 implanted in the subject, the power source 14 can be activated at Step 36. Activation of the power source 14 causes one or more therapy signals, having desired power and stimulation parameters, to be delivered to the neuromuscular stimulator 16. In some instances, the therapy signal(s) (e.g., an electrical signal) may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz, with a pulse-width of about 10 to about 1000 microseconds. The type of stimulation may vary and involve different waveforms known to the skilled artisan.

Depending upon the desired treatment regimen, the therapy signal(s) is/are relayed to the electrode 24. The therapy signal(s) can be relayed to the electrode 24 for a time and in an amount sufficient to displace the posterior base of the tongue in an anterior direction, which opens the oropharyngeal airway to the laryngeal introitus. Delivery of the therapy signal(s) to the target tissue can be done, for example, while the subject is sleeping. In patients with OSA, the posterior base of the tongue can fall backwards and obstruct breathing, especially when individuals lay flat on their backs. Therapy signal(s) from the neuromuscular stimulator 16 can be delivered to the target tissue on a continuous, periodic, or an as-needed basis to displace the posterior base of the tongue in an anterior direction (and/or change the surface morphology of the posterior tongue base to allow and increase oropharyngeal airway volume) while the subject is sleeping. This prevents obstruction of the airway during sleep by ensuring that airflow through the airway of the subject is properly maintained. Additionally or optionally, the therapy signal(s) can be relayed to the electrode 24 to achieve selective muscle activation; that is, targeted activation of less than all of the muscles comprising the anterior lingual musculature 12. Advantageously, selective stimulation of the anterior lingual musculature 12 can prevent or mitigate dysarthria.

Another aspect of the present disclosure can include a method 70 (FIG. 11) for treating OSA in a subject. The method 70 can generally include the steps of: providing a closed-loop system 50 (Step 72); implanting the system into a subject suffering from OSA (Step 74); generating a sensor signal based on a detected at least one physiological parameter or related symptom associated with OSA (Step 76); and delivering a therapy signal, by the system, to a target tissue to treat the OSA (Step 78). Steps 76-78 can be repeated for a desired period of time to treat the OSA (Step 80). The closed-loop system 50 provided at Step 72 can be identically or similarly constructed as the system shown in FIG. 3 and described above. For example, the system 50 shown in FIG. 3 can be configured to include multiple electrodes 24 and sensing components 52, which may limit total extrinsic and intrinsic tongue contraction and assist in anterior-superior elevation of the suprahyoid muscles (and thus the hyoid bone) to open the laryngeal introitus. At Step 74, the system 50 can be implanted in the subject.

At Step 76, a sensor signal can be generated by the sensing component 52 in response to at least one physiological parameter or a related symptom associated with OSA detected by the sensing component. Where the sensing component 52 is an EMG electrode, for example, the activity of one or more muscles of the anterior lingual musculature (e.g., a genioglossus muscle or a suprahyoid muscle) can be detected. A detected decrease in muscle activity (relative to a control or baseline level) may cause the sensing component 52 to generate a corresponding sensor signal, which is then relayed to the controller 26 and/or the power source 14.

In response to the generated sensor signal, the system 50 can cause a therapy signal (or signals) to be delivered to the electrode 24 (Step 78). The controller 26 can then control operation of the neuromuscular stimulator to adjust application of the therapy signal(s) to the first target tissue in response to the sensor signal. For example, the therapy signal(s) can be relayed to the electrode 24 for a time and in an amount sufficient to displace the posterior base of the tongue in an anterior direction, which opens the oropharyngeal airway to the laryngeal introitus. Delivery of the therapy signal(s) to the target tissue can be done, for example, while the subject is sleeping. In patients with OSA, the posterior base of the tongue can fall backwards and obstruct breathing, especially when individuals lay flat on their backs. Therapy signal(s) from the neuromuscular stimulator 16 can be delivered to the first target tissue on a continuous, periodic, or an as-needed basis to displace the posterior base of the tongue in an anterior direction (and/or change the surface morphology of the posterior tongue base to allow and increase oropharyngeal airway volume) while the subject is sleeping. This prevents obstruction of the airway during sleep by ensuring that airflow through the airway of the subject is properly maintained. Additionally or optionally, the therapy signal(s) can be relayed to the electrode 24 to achieve selective muscle activation; that is, targeted activation of less than all of the muscles comprising the anterior lingual musculature. Advantageously, selective stimulation of the anterior lingual musculature can prevent or mitigate dysarthria. It will be appreciated that although the method 70 is described in terms of unilateral stimulation, the method can also be performed using bilateral stimulation (e.g., stimulating two muscles simultaneously or in sequence).

Figure 11:
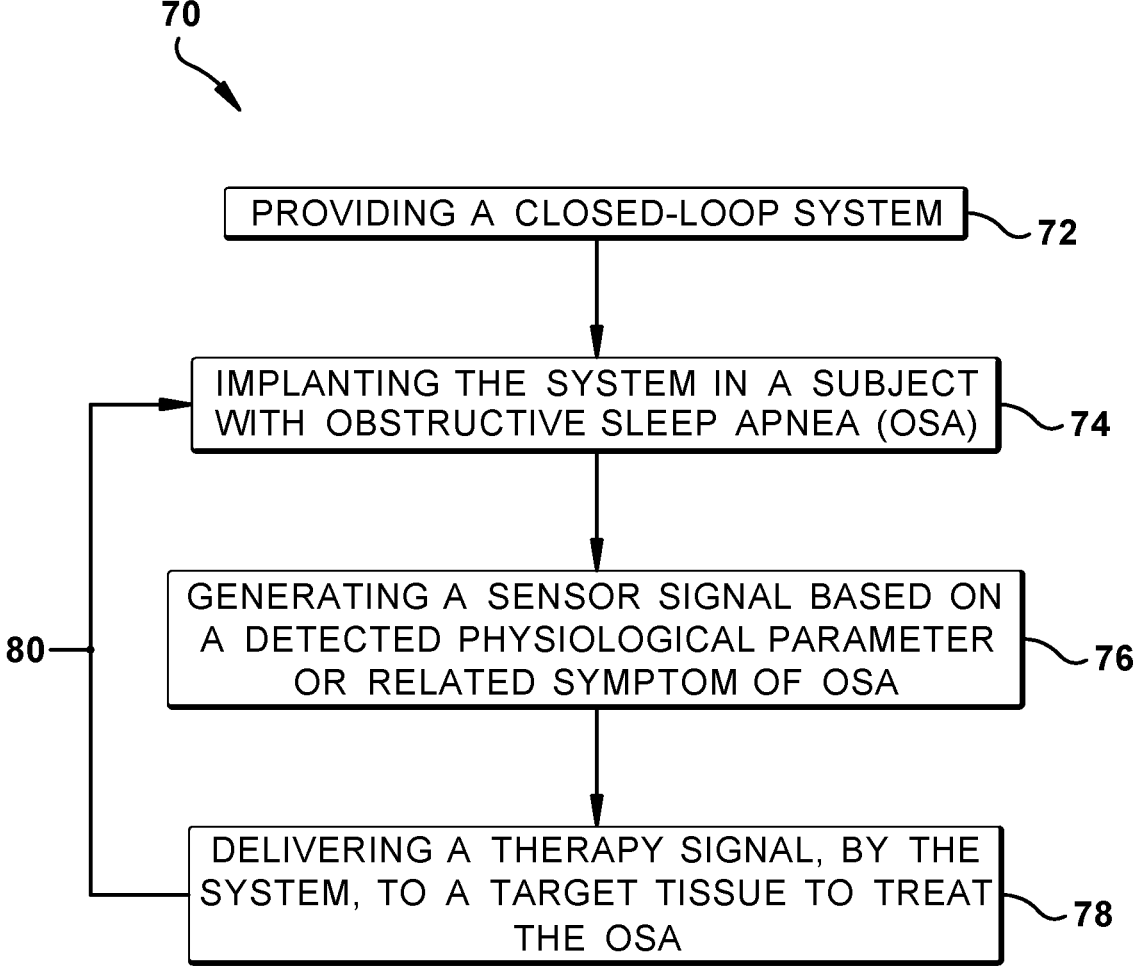
FIG. 11 is a process flow diagram illustrating a method for treating OSA in a subject according to another aspect of the present disclosure.

As shown in FIG. 11, Steps 76-78 can be repeated for a period of time to treat the OSA. Advantageously, the method 70 provides a minimally invasive, automatic, and aesthetically acceptable treatment modality for OSA that is continually titrated to optimize its efficacy based on continuous physiological feedback, thereby enabling a high degree of patient-specific customization.

Another aspect of the present disclosure includes a method for treating sleep disordered breathing (SBD) in a subject by using an electromyogram (EMG) signal to initiate stimulation of a muscle that controls the upper airway and/or the tongue of the subject (also referred to herein as an "upper airway muscle"), such as the genioglossus muscle. In certain embodiments, the EMG activity of an upper airway muscle can be used as a biomarker for respiration and electrical stimulation of the upper airway muscle can be triggered or predicted from an EMG signal of the upper airway muscle during certain periods of the subject's respiratory cycle. Preferably, a single neurostimulator is used to record an EMG signal from the upper airway muscle and to initiate stimulation to neuromuscular tissue of the upper airway muscle based on the recorded EMG signal to decrease the subject's airway resistance to treat the subject's SBD. Non-limiting examples of SBDs are increased upper airway resistance including snoring; upper airway resistance syndrome (UARS); and sleep apnea. Sleep apnea can include OSA, central sleep apnea (CSA), and mixed sleep apnea.

Figure 3:
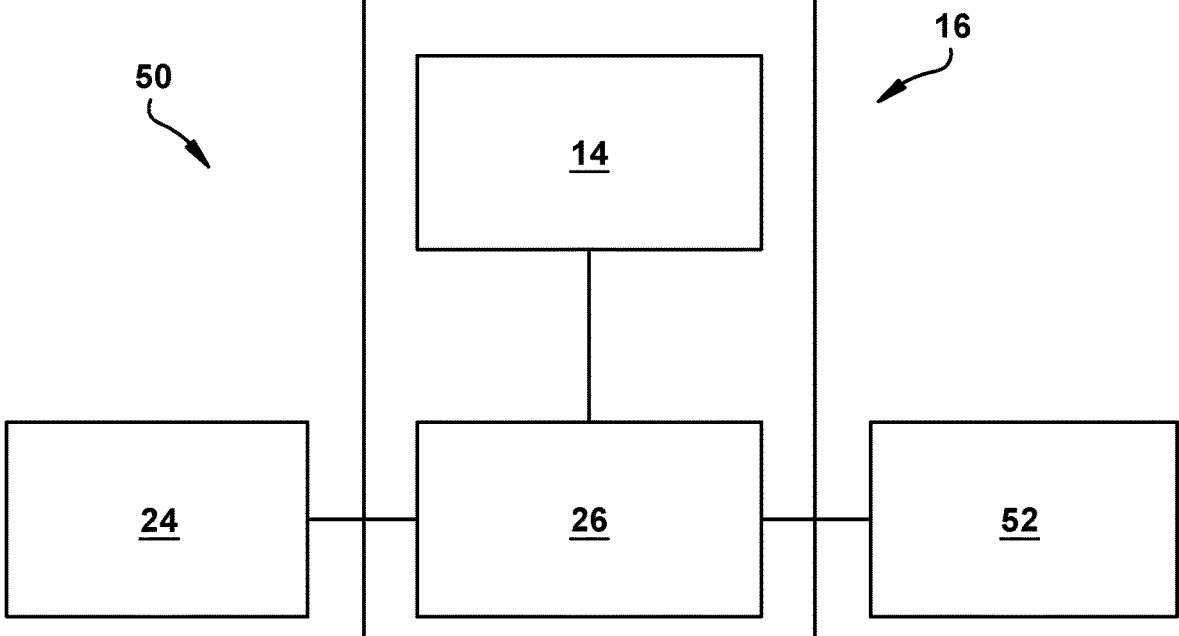
FIG. 3 is a schematic illustration of a closed-loop system for treating OSA according to another aspect of the present disclosure.
Figure 13:
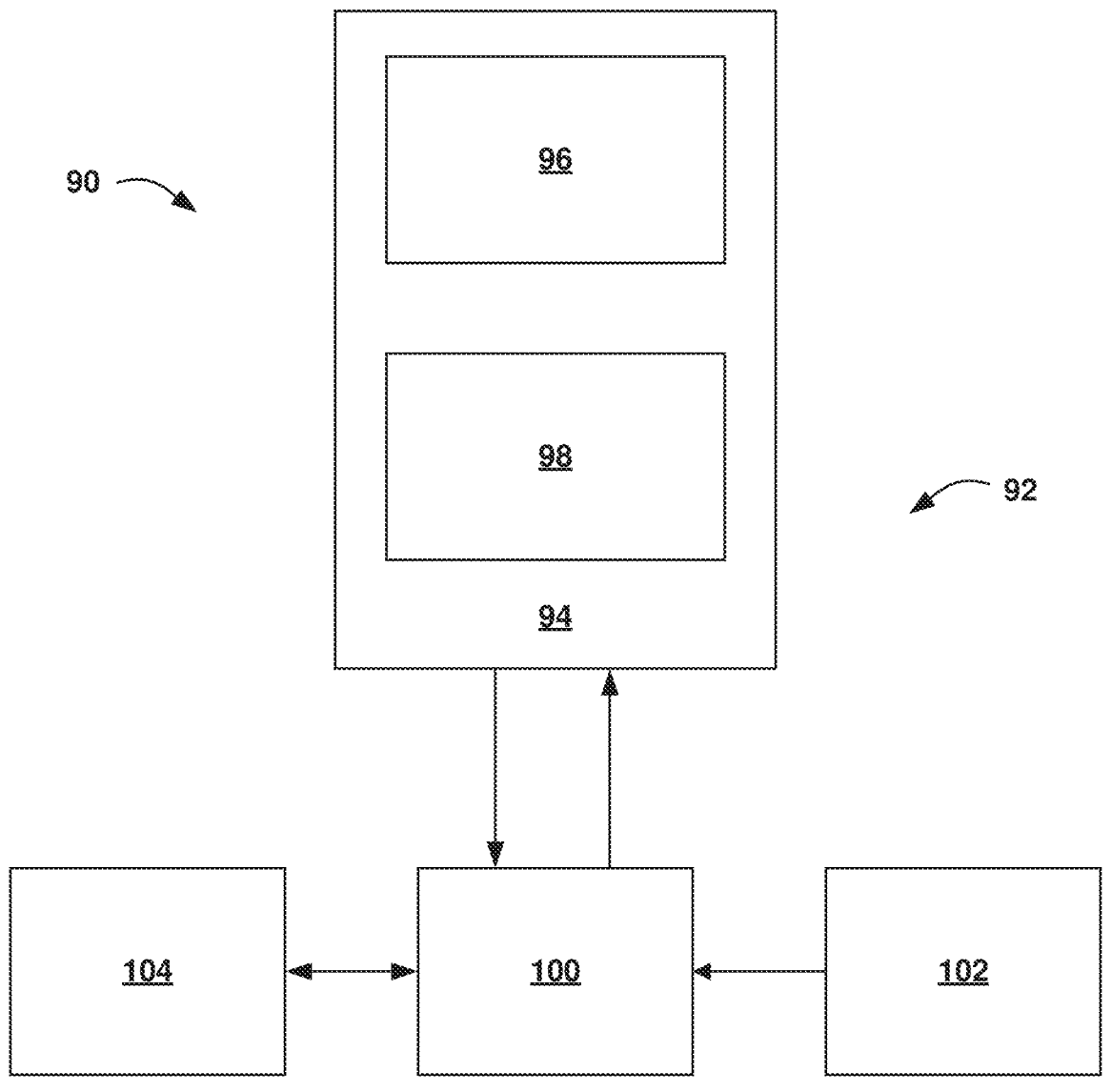
FIG. 13 is a block diagram of a neurostimulation system according to an aspect of the present disclosure.

Referring to FIG. 12, method 80 can include obtaining a neurostimulation system comprising a neurostimulator having a stimulating electrode and an EMG sensor located thereon (step 82). In certain embodiments, the EMG sensor is located on a separate device than the neurostimulator. The neurostimulator can be part of a closed loop system 50 as shown in FIG. 3 or a neurostimulation system as schematically depicted in FIG. 13 and described below. Method 80 can further include positioning the neurostimulator so that the stimulating electrode and the EMG sensor are in electrical communication with an upper airway muscle of the subject, such as the genioglossus muscle (step 84). The stimulating electrode can be positioned in direct electrical communication with the upper airway muscle such that the upper airway muscle is the target site as opposed to a proximal site that innervates the upper airway muscle or a muscle or nerve that is anatomically adjacent to the upper airway muscle. In such embodiments, the stimulating electrode is adjacent to the upper airway muscle to directly stimulate the upper airway muscle. Similarly, the EMG sensor can be positioned in direct electrical communication with the upper airway muscle such that the upper airway muscle is the target sensing site as opposed to a proximal site that innervates the upper airway muscle or a muscle or nerve that is anatomically adjacent to the the upper airway muscle. In such embodiments, the EMG sensor is adjacent to the upper airway muscle such that the EMG sensor is receiving input directly from the upper airway muscle as opposed to receiving input from a proximal site that innervates or is anatomically adjacent to the upper airway muscle. At step 86, method 80 can include monitoring the subject for an EMG signal indicative of a certain period of the subject's respiratory cycle by sensing EMG activity of the upper airway muscle. At step 88, method 80 can include activating the neurostimulator to provide electrical stimulation to the upper airway muscle in response to the EMG signal to decrease the subject's airway resistance and treat the SBD. Steps 86-88 can be repeated for a desired period of time to treat the SBD.

Referring to FIG. 13, neurostimulation system 90 can include neurostimulator 92 that is at least one lead 94 having stimulating electrode 96 and EEG sensor 98 located thereon. The neurostimulator is illustrated in other figures as being a lead but the neurostimulator could have other configurations. Neurostimulator 92 can also include an interface circuit and an amplifier (not shown), and a controller 100. The interface circuit can receive EMG activity input from EMG sensor 98 and can send an EMG signal to the amplifier. The amplifier can supply an amplified and filtered EMG signal to controller 100. Controller 100 can process the amplified and filtered EMG signal to determine whether the EMG signal is indicative of a certain period of a subject's respiratory cycle such that the upper airway muscle should be stimulated. For example, the EMG signal can represent a spike or increase in EMG activity compared to a baseline level that may indicate the onset of inspiration; a gradual increase in EMG activity compared to a baseline level that may indicate an imminent onset of inspiration; or another detectable feature of EMG activity of the upper airway muscle indicative of a certain period of the subject's respiratory cycle, such as before, during or after the onset of the expiration phase. The EMG activity can represent a spike in upper airway muscle activity or an absence of upper airway muscle activity.

When controller 100 detects an EMG signal indicative of a certain period of a subject's respiratory cycle such that the upper airway muscle should be stimulated, it can output a trigger signal to the interface circuit. Once the interface circuit receives the trigger signal, it can output a stimulation signal to electrode 96 to stimulate to the upper airway muscle. Controller 100 can also be programmed to define a threshold level of EMG activity or a delta of a baseline level (e.g. an amplitude limit) of EMG activity. When this threshold level or delta value is reached, the controller can send a trigger signal to the interface circuit to output a stimulation signal to the stimulating electrode.

Neurostimulation system 90 can include a power supply 102 and an external processor 104. The power supply can be an internal power supply, as depicted in FIG. 13, such as a rechargeable battery that is rechargeable from outside the subject's body via inductive or radiofrequency coils. Alternatively, the power supply can be an external power supply. A two-way communication link can be associated with controller 100 for communication between controller 100 and external processor 104. External processor 104 can have the capability to receive data from controller 100 and transmit data to controller 100 via the communication link. In this manner, a clinician can evaluate physiological data and system data accumulated by neurostimulator 92. Such data can be stored on a memory device (not shown) of the neurostimulation system.

Figure 14:
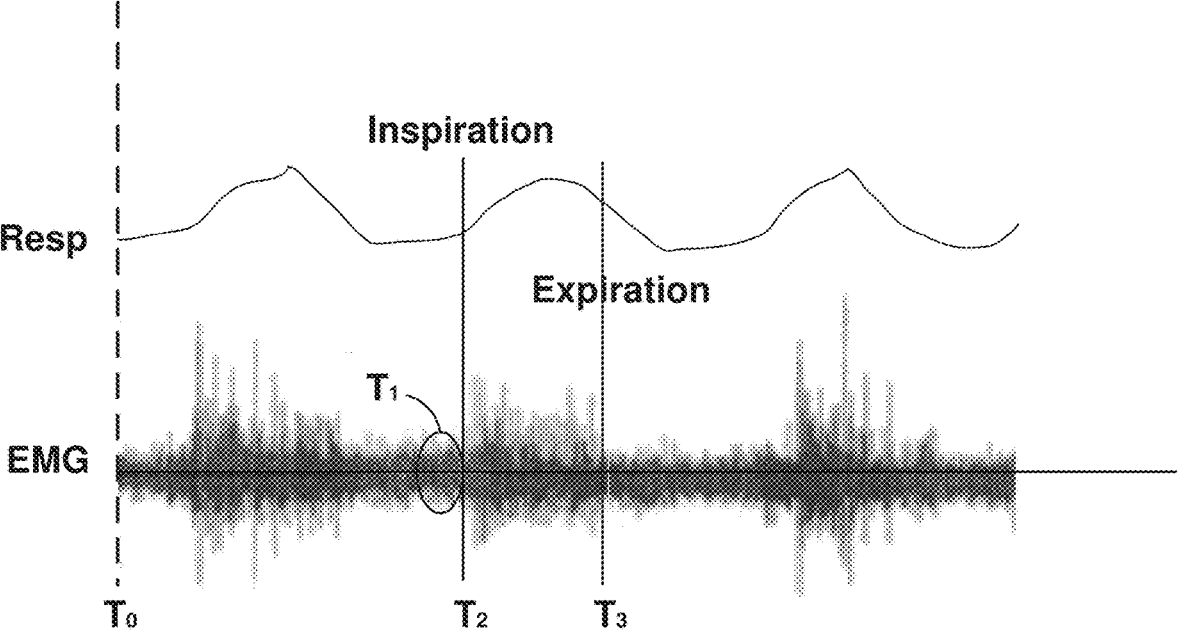
FIG. 14 is a graphic illustration of airflow (Resp) during an exemplary subject's respiratory cycle and the corresponding EMG activity measured at the upper airway muscle according to an aspect of the present disclosure.

FIG. 14 is a graphic illustration of airflow (Resp) during an exemplary subject's respiratory cycle and the corresponding EMG activity measured at the upper airway muscle. In an embodiment, the EMG sensor can continuously monitor the EMG activity of an upper respiratory muscle of a given subject beginning at time to. For example, at the onset of the inspiration phase of respiration at time t2, the controller can detect EMG activity indicative of the onset of the inspiration phase of respiration from the signals supplied by the EMG sensor. For example, there can be a spike in EMG activity for a given subject upon the onset of the inspiration phase compared to a baseline level. At this point, the controller can send a control signal to a stimulating electrode to electrically stimulate the upper airway muscle to decrease airway resistance to open the subject's airway. There can also be a gradual increase in EMG activity compared to a baseline level for a given subject prior to the onset of the inspiration phase at $t_1$ that the controller can detect from the signals supplied by the EMG sensor. At this point, the controller can send a control signal to the stimulating electrode to electrically stimulate the upper airway muscle. At time $t_3$, the subject's respiratory cycle converts from the inspiration phase to the expiration phase. The controller can detect EMG activity indicative of the onset of the expiration phase of respiration, such as a change in EMG activity compared to a baseline level, from the signals supplied by the EMG sensor. At this point, the controller can send a control signal to the stimulating electrode to electrically stimulate the upper airway muscle. The above-described times when an upper airway muscle is electrically stimulated are only exemplary and the upper airway muscle can be electrically stimulated during any one or more combinations of these times.

The upper airway muscle can be electrically stimulated at other times indicative of different periods of the respiratory cycle based on the EMG activity of the upper airway muscle for a given subject such that the electrical stimulation decreases airway resistance to open the subject's airway. For example, based on the EMG activity of the upper airway muscle for a given subject, the muscle can be electrically stimulated at the onset of the inspiration phase of respiration, prior to the inspiration phase but after the expiration phase, at the onset of the expiration phase, during the expiration phase, after the expiration phase but prior to the inspiration phase, or any combination thereof. The electrical stimulation can end at an onset of an exhalation phase of the respiratory cycle or at an end of an inhalation phase of the respiratory cycle.

Since the electrical stimulation should result in opening of the patient's airway, the electrical stimulation can be provided at a time that allows for the airway resistance to decrease in order to open the subject's airway. The upper airway muscle also can be electrically stimulated after a pre-set time period elapses after detection of certain EMG activity.

The specific sleep EMG activity of an upper airway muscle during different periods of a respiratory cycle varies from subject to subject as does the onset and duration of respiration phases, such as inspiration and expiration. As such, the subject can be initially monitored during sleep to determine the subject's specific sleep respiratory cycle pattern such as the onset and duration of inspiration and expiration. Based on this pattern and in conjunction with the corresponding EMG pattern of activity, the controller can be programmed with a subject-specific algorithm to deliver electrical stimulation at certain periods of the respiratory cycle for a given subject in order to open the subject's airway. The controller can monitor the EMG activity of the upper airway muscle continuously or periodically.

Another method that may be used to initiate monitoring of EMG activity indicative of a certain period of a respiratory cycle during sleep is through the use of an algorithm to monitor the cyclic nature of EMG activity during a respiratory cycle for a given subject. The controller can learn the pattern of the respiratory cycle during sleep for a given patient based on the EMG activity of the upper airway muscle. The controller can then use this information to determine or predict when to provide a control signal to a stimulating electrode to stimulate the upper airway muscle. For example, the EMG activity of a certain number of respiratory cycles of a subject can be recorded and averaged to determine when the subject starts an inspiration phase and an expiration phase and the duration of these phases. Based on this information, the controller can predict when to initiate stimulation to decrease the subject's airway resistance to open the subject's airway to treat the SDB.

In some instances, a trans-mandibular surgical approach can be used to implant the system 50 or components thereof, such as a neurostimulator, as described above. A variety of trans-mandibular surgical approach options may be used, such as a submental approach or an intraoral bucca-gingival sulcus approach. Generally speaking, a submental approach allows for other adjunctive procedures including, but not limited to, cervical liposuction (e.g., for effacement of platysmal banding), elevation of hyoid positioning, and mandibular distal bone advancement for aesthetic purposes and/or functionally repositioning the anterior lingual musculature. Unlike the submental approach, an intraoral approach does not produce a facial scar. A trans-mandibular surgical approach can be performed under local anesthetic or in an outpatient setting; however, it will be appreciated that general anesthetic may alternatively be used as patients may be more comfortable and the patient's airway is better protected.

Whether a submental or intraoral bucca-gingival sulcus approach is used, the dissection can be carried out to the level of the periosteum overlying the mentum of the mandible 28. Surgical awareness is highlighted at this time in an effort to preserve and not traumatize the mental nerves (not shown). The mental nerves exit at the mid-vertical level of the mandible, between the region of the first and second pre-molars bilaterally. Like many surgeries in the head and neck, preservation of a nerve (or nerves) along with strict attention to hemostasis are key features of a successful operation. In making the gingivo-labial sulcus incision, for example, it can be important to leave an adequate cuff of mucosa along with a sufficient portion of the mentalis muscle (not shown) for later resuspension. Doing so can avoid lower-lip ptosis.

In one example, a submental approach can be used to implant the system 50 or components thereof, such as a neurostimulator, as described above in a subject suffering from SDB or OSA. First, an external submental crease incision (not shown) can be made. A subperiosteal dissection can then be made to elevate the periosteum and protect the mental nerves. At this point, a surgical mark can be made at the midline of the bony mentum. One or more drill holes (not shown) can be made above the inferior edge of the mentum, and on either side of the midline. For example, multiple drill holes can be made about 1 cm above the inferior edge of the mentum, and about 1.5 cm on either side of the midline. The diameter of each drill hole should be sufficient to pass the leads 22 associated with the at least one electrode 24 and the sensing component 52 of the system 50 through both cortices of the mandible 28 into electrical communication with first and second target tissues, respectively.

In another example, an intraoral bucca-gingival sulcus approach can alternatively be used to implant the system 50 or components thereof, such as a neurostimulator, as described above. Subperiosteal dissection can be carried out laterally to identify the mental nerves. The foramina (not shown) of the mental nerves are generally found between the first and second premolar teeth at the level of the origin of the mentalis muscle, or 2-4 mm below the level of the bicuspid premolar teeth apices. The foramina are situated deep to the midportion of the depressor anguli oris. Dissection can occur inferolaterally to allow for a longer osteotomy and thereby prevent unsightly mandibular notching. During dissection, the periosteum at the inferior rim of the mentum can be left intact. Next, the skeletal midline can be aligned with the overlying soft tissue corollary. A sagittal saw with a 30-degree bend can then be used to facilitate an even cut while minimizing soft tissue trauma. Lateral cuts can be made about 4-5 mm below the foramina to compensate for the path of the inferior alveolar nerve.

The foregoing surgical approaches can include implantation of a chin implant 54 (such as the one described above) in instances where a subject desires an aesthetic change to their anterior mandibular profile. Alternatively, if a subject does not desire a change in their anterior mandibular profile, a relatively small or low-profile neuromuscular stimulator 16 that does not cause any profile changes can be used. For example, a neuromuscular stimulator 16 can be sized and dimensioned for placement within a drilled sulcus such that attachment of the neuromuscular stimulator therein does not interfere with the anterior mandibular profile of the subject.

Regardless of the trans-mandibular surgical approach used, the system 50 or components thereof, such as a neurostimulator, as described above can be implanted so that the electrode 24 and the sensing component 52 are in electrical communication with target tissue, such as first and second target tissues, respectively (e.g., the electrodes can be placed directly on and/or within the first and second target tissue). The first and second target tissues can be the same or different. In some instances, the electrode 24 can be placed into electrical communication with a first target tissue comprising one or more muscles of the anterior lingual musculature 12 (e.g., one or a combination of suprahyoid muscles). In one example, the electrode 24 and/or the sensing component 52 can be placed into electrical communication with a genioglossus muscle (not shown). In another example, the electrode 24 and/or the sensing component 52 can be placed into electrical communication with an anterior belly digastric muscle (not shown). In another example, the electrode 24 and/or the sensing component 52 can be placed into electrical communication with a hyoglossus muscle (not shown). In another example, the electrode 24 and/or the sensing component 52 can be placed into electrical communication with a mylohyoid muscle (not shown).

Proper positioning of the electrode 24 can be confirmed by delivering test signals to the electrode and then noting if the test signals result in anterior displacement of the posterior base of the tongue. Once the electrode 24 is properly positioned, the remainder of the system 50 can be securely affixed to the subject. For example, the implant body 56 of a chin implant 54 can be securely affixed (e.g., with bone screws) into the external cortex of the mandible 28. Once the system 50 is securely implanted in the subject, the soft tissue can be closed in layers while paying special attention to the reattachment of the mentalis muscle to avoid ptotic lower lip. The soft tissue can then be re-draped with tape and the procedure completed. Overall, the surgical implant procedure can take about 15 minutes to complete.

If it has not been done so already, the power source 14 can be associated with the subject so that the power source is in electrical communication with the neuromuscular stimulator 16. With the system 50 or components thereof, such as a neurostimulator, as described above implanted in the subject, the power source 14 can then be activated. Activation of the power source 14 enables the sensing component 52 to detect at least one physiological parameter or a related symptom associated with OSA. Activation of the power source 14 also permits one or more therapy signals having desired power and stimulation parameters to be delivered to the electrode 24. In some instances, the therapy signal(s) (e.g., an electrical signal) may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz, with a pulse-width of about 10 to about 1000 microseconds. The type of stimulation may vary and involve different waveforms known to the skilled artisan.

It will be appreciated that the present disclosure may also be an adjunct to other mechanical orthognathic maneuvers to sections of the mandible that have tongue muscle attachments to them.

From the above description of the present disclosure, those skilled in the art will perceive improvements, changes and modifications. For example, it will be appreciated that a subject may be placed in a sleep lab after surgery so that particular settings (e.g., stimulation parameters) of the system 10 and 50 can be optimized based on the needs of the subject. Additionally, it will be appreciated that, depending upon the static placement of the sublingual muscles, a preoperative decision can be made (e.g., based on soft and hard tissue cephalometrics) to reposition the anterior mentum and lingual muscle attachments to statically permit further advancement of the tongue base in concert with electrical stimulation of the sublingual muscles. Such improvements, changes, and modifications are within the skill of those in the art and are intended to be covered by the appended claims. All patents, patent applications, and publication cited herein are incorporated by reference in their entirety.

The following is claimed:

1. A method for treating disordered breathing that occurs during sleep in a subject comprising:

positioning a neurostimulator in a head of the subject, the neurostimulator comprising a stimulating electrode and an electromyogram (EMG) sensor, wherein the neurostimulator is positioned such that the stimulating electrode and the EMG sensor are both in electrical communication with a muscle that controls a tongue of the subject and/or both in electrical communication with a nerve that controls the muscle of the tongue;

for a given respiratory cycle that includes an inspiration phase and an expiration phase, the expiration phase occurring subsequent to the inspiration phase and the inspiration phase following an expiration phase of a respiratory cycle preceding the given respiratory cycle:

after the expiration phase of the respiratory cycle immediately preceding the given respiratory cycle but prior to the onset of the inspiration phase of the given respiratory cycle, sensing EMG activity of the muscle of the tongue with the implanted EMG sensor and detecting an EMG signal indicative of an upcoming onset of the inspiration phase of the given respiratory cycle; and activating the neurostimulator to provide an electrical signal to the muscle of the tongue or nerve at the onset of or during the inspiration phase of the given respiratory cycle in response to the EMG signal to decrease the subject's airway resistance and treat the disordered breathing.

2. The method of claim 1, wherein the electrical stimulation ends at an onset of the expiration phase of the given respiratory cycle.

3. The method of claim 1, wherein the EMG signal indicative of the onset of the inspiration phase is sensed prior to the onset of the inspiration phase of the given respiratory cycle but after an expiration phase of a respiratory cycle preceding the given respiratory cycle.

4. The method of claim 1, further comprising monitoring the sensed EMG activity for another EMG signal indicative of an onset of the expiration phase of the given respiratory cycle.

5. The method of claim 1, wherein the electrical stimulation ends at an end of the inspiration phase of the given respiratory cycle.

6. The method of claim 1, wherein the stimulating electrode and the EMG sensor are both in electrical communication with a genioglossus muscle of the tongue of the subject or both in electrical communication with a nerve that controls the genioglossus muscle.

7. The method of claim 1, wherein the stimulating electrode is carried by a first lead and the neurostimulator further comprises a second lead.

8. The method of claim 1, wherein the neurostimulator comprises two or more electrodes and positioning the neurostimulator comprises placing the two or more electrodes bilaterally into electrical communication with the tongue.

9. The method of claim 1, wherein providing the electrical signal to the nerve comprises electrically stimulating the hypoglossal nerve and/or its distal arborizing branches at or near its neuromuscular junction.

10. The method of claim 1, wherein the stimulating electrode is carried by a lead, and the lead of the neurostimulator is in direct electrical communication with a power source.

11. The method of claim 1, wherein the stimulating electrode is carried by a lead, and the lead of the neurostimulator includes an anchoring element.

12. The method of claim 1, wherein the neurostimulator comprises at least two leads, each of the leads having at least two electrodes and positioning the neurostimulator comprises positioning the at least two leads at different spatial locations.

13. The method of claim 1, wherein the EMG signal indicative of the onset of the inspiration phase of the given respiratory cycle comprises an increase in EMG activity compared to a baseline level of the EMG activity, the increase in EMG activity occurring prior to the onset of the inspiration phase of the given respiratory cycle.

14. A method for treating disordered breathing that occurs during sleep in a subject, the subject having a first respiratory cycle and a second respiratory cycle subsequent to the first respiratory cycle and each of the first and second respiratory cycles having an inspiration phase followed by an expiration phase, the method comprising:

positioning a neurostimulator in a head of the subject, the neurostimulator comprising a stimulating electrode and an electromyogram (EMG) sensor, wherein the neurostimulator is positioned such that the stimulating electrode and the EMG sensor are both in electrical communication with a muscle that controls a tongue of the subject and/or both in electrical communication with a nerve that controls the muscle of the tongue;

after the expiration phase of the first respiratory cycle but prior to the onset of the inspiration phase of the second respiratory cycle, sensing EMG activity of the muscle of the tongue with the implanted EMG sensor and detecting an EMG signal indicative of an upcoming onset of the inspiration phase of the second respiratory cycle, wherein the EMG signal comprises an increase in EMG activity compared to a baseline level of the EMG activity, the increase in EMG activity occurring prior to the onset of the inspiration phase of the second respiratory cycle; and activating the neurostimulator to provide an electrical signal to the muscle of the tongue or nerve at or just prior to the onset of the inspiration phase of the second respiratory cycle in response to the EMG signal to decrease the subject's airway resistance and treat the disordered breathing.

15. The method of claim 14, wherein the electrical stimulation ends at an onset of the expiration phase of the second respiratory cycle.

16. The method of claim 14, wherein the EMG signal indicative of the onset of the inspiration phase is sensed prior to the onset of the inspiration phase of the second respiratory cycle but after the expiration phase of the first respiratory cycle.

17. The method of claim 14, further comprising monitoring the sensed EMG activity for another EMG signal indicative of an onset of the expiration phase of the second respiratory cycle.

18. The method of claim 14, wherein the electrical stimulation ends at an end of the inspiration phase of the second respiratory cycle.

19. The method of claim 14, wherein the stimulating electrode and the EMG sensor are both in electrical communication with a genioglossus muscle of the tongue of the subject or both in electrical communication with a nerve that controls the genioglossus muscle.

20. The method of claim 14, wherein the stimulating electrode is carried by a first lead and the neurostimulator further comprises a second lead.

21. The method of claim 14, wherein the neurostimulator comprises two or more electrodes and positioning the neurostimulator comprises placing the two or more electrodes bilaterally into electrical communication with the tongue.

22. The method of claim 14, wherein providing the electrical signal to the nerve comprises electrically stimulating the hypoglossal nerve and/or its distal arborizing branches at or near its neuromuscular junction.

23. The method of claim 14, wherein the stimulating electrode is carried by a lead, and the stimulating electrode is carried by a lead, and the lead of the neurostimulator is in direct electrical communication with a power source.

24. The method of claim 14, wherein the stimulating electrode is carried by a lead, and the lead of the neurostimulator includes an anchoring element.

25. The method of claim 14, wherein the neurostimulator comprises at least two leads, each of the leads having at least two electrodes and positioning the neurostimulator comprises positioning the at least two leads at different spatial locations.

* * * * *